United States Patent
Beier et al.

(10) Patent No.: US 8,273,759 B2
(45) Date of Patent: Sep. 25, 2012

(54) FUNGICIDE HETEROCYCLYL-PYRIMIDINYL-AMINO DERIVATIVES

(75) Inventors: Christian Beier, Saint Genis-Iaval (FR); Pierre-Yves Coqueron, Lyons (FR); Ralf Dunkel, Lyons (FR); Pierre Genix, Lyons (FR); Jörg Greul, Leichlingen (DE); Marie-Claire Grosjean-Cournoyer, Curis au Mont d'Or (FR); Emmanuelle Hilt, Dizimieu (FR); Philippe Rinolfi, Châtillon d'Azergues (FR); Arnd Voerste, Köln (DE); Jean-Pierre Vors, Sainte Foy lès Lyon (FR)

(73) Assignee: Bayer Cropscience AG (DE)

( * ) Notice: Subject to any disclaimer, the term of this patent is extended or adjusted under 35 U.S.C. 154(b) by 198 days.

(21) Appl. No.: 12/451,941

(22) PCT Filed: Jun. 6, 2008

(86) PCT No.: PCT/EP2008/057126
§ 371 (c)(1),
(2), (4) Date: Mar. 11, 2010

(87) PCT Pub. No.: WO2008/148889
PCT Pub. Date: Dec. 11, 2008

(65) Prior Publication Data
US 2010/0204229 A1    Aug. 12, 2010

(30) Foreign Application Priority Data
Jun. 8, 2007 (EP) .................... 07356077

(51) Int. Cl.
*A01N 43/54* (2006.01)
(52) U.S. Cl. .................. 514/275; 544/331
(58) Field of Classification Search .......... 544/331
See application file for complete search history.

(56) References Cited

FOREIGN PATENT DOCUMENTS

| WO | WO 03/029249 | 4/2003 |
|----|--------------|--------|
| WO | WO 03/049542 | 6/2003 |
| WO | WO 2004/065378 | 8/2004 |
| WO | WO 2004/084634 | 10/2004 |
| WO | WO 2005/019211 | 3/2005 |

OTHER PUBLICATIONS

Christian Pillonel, Evaulation of phenylaminopyrimidines as antifungal protein kinase inhibitors, Pest Management Science, vol. 61, No. 11, 2005, pp. 1069-1076, XP002462829, ISSN: 1526-498X.
Kreutzberger, A., et al. Antimycotic substances, XX. Fluorinated 2-(4-toluidino) pyrimidines, Journal of Heterocyclic Chemistry, vol. 22, No. 1, 1985, pp. 101-103, ISSN: 0022-152X.

*Primary Examiner* — James O Wilson
*Assistant Examiner* — Brian McDowell
(74) *Attorney, Agent, or Firm* — Ostrolenk Faber LLP

(57) ABSTRACT

The present invention relates to heterocyclyl-pyrimidinyl-amino derivatives of formula (I)

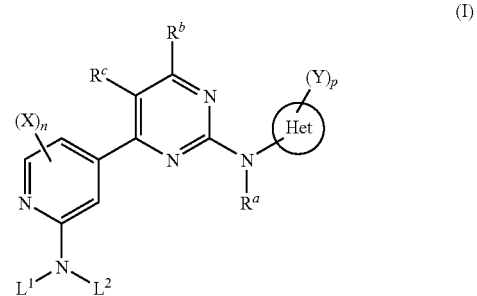

heterocyclyl-pyrimidinyl-amino derivatives of formula (I) wherein Het, Y, p, $R^a$, $R^b$, $R^c$, X, n, $L^1$ and $L^2$ represent various substituents, their process of preparation, preparation intermediate compounds, their use as fungicide active agents, particularly in the form of fungicide compositions, and methods for the control of phytopathogenic fungi, notably of plants, using these compounds or compositions.

15 Claims, No Drawings

FUNGICIDE HETEROCYCLYL-PYRIMIDINYL-AMINO DERIVATIVES

CROSS-REFERENCE TO RELATED APPLICATION(S)

The present application is a 35 U.S.C. §371 national phase conversion of PCT/EP2008/057126 filed 6 Jun. 2008, which claims priority of European Application No. 07356077.3 filed 8 Jun. 2007.

The present invention relates to heterocyclyl-pyrimidinyl-amino derivatives, their process of preparation, preparation intermediate compounds, their use as fungicide active agents, particularly in the form of fungicide compositions, and methods for the control of phytopathogenic fungi, notably of plants, using these compounds or compositions.

In international patent application WO-2005/019211, there are described some compounds having both a biaryl moiety and a heterocyclic moiety that can be used as fungicide agents. Even if some of these compounds may possess structural similarities with the compounds according to the invention, this document does not disclose nor suggest the compounds according to the invention. Apart, 4-[2-(ethylamino)-4-pyridinyl]-N-[5-(1-piperazinyl)-2-pyridinyl]-2-pyrimidinamine has been disclosed in international patent application WO-2004/065378, it may be useful as inhibitor of the cellular proliferation. This compound has been excluded from the scope of the present invention.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining effectiveness at least equivalent to the already known compounds. We have now found a new family of compounds which possess the above mentioned effects or advantages.

Accordingly, the present invention provides heterocyclyl-pyrimidinyl-amino derivatives of formula (I)

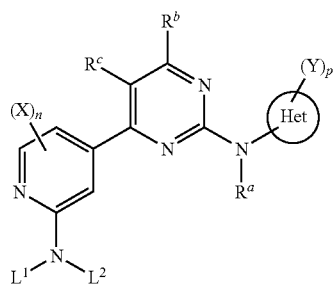

(I)

wherein
Het represents a saturated or unsaturated, aromatic or non-aromatic 4-, 5-, 6- or 7-membered heterocycle comprising up to four heteroatoms which may be the same or different;
Y independently represents a halogen atom, a nitro group, a hydroxy group, an oxo group, a cyano group, an amino group, a sulphenyl group, a pentafluoro-$\lambda^6$-sulphenyl group, a formyl group, a formyloxy group, a formylamino group, a carbamoyl group, a N-hydroxycarbamoyl group, a carbamate group, a (hydroxyimino)-$C_1$-$C_6$-alkyl group, a $C_1$-$C_8$-alkyl, a tri($C_1$-$C_8$-alkyl)silyl, a substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, a $C_1$-$C_8$-halogenoalkyl having 1 to 5 halogen atoms, a $C_1$-$C_8$-halogenocycloalkyl having 1 to 5 halogen atoms, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulphenyl, a $C_1$-$C_8$-halogenoalkylsulphenyl having 1 to 5 halogen atoms, a $C_1$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms, a $C_1$-$C_8$-alkylaminosulfamoyl, a di-$C_1$-$C_8$-alkylaminosulfamoyl, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_8$-alkyl, a 2-oxopyrrolidin-1-yl, substituted or non-substituted (benzyloxyimino)-$C_1$-$C_6$-alkyl, substituted or non-substituted $C_1$-$C_8$-alkoxyalkyl, substituted or non-substituted $C_1$-$C_8$-halogenoalkoxyalkyl having 1 to 5 halogen atoms, substituted or non-substituted benzyloxy, substituted or non-substituted benzylsulphenyl, substituted or non-substituted benzylamino, substituted or non-substituted phenoxy, substituted or non-substituted phenylsulphenyl, or substituted or non-substituted phenylamino;
p represents 0, 1, 2, 3, 4, 5 or 6;
$R^a$ represents a hydrogen atom, a cyano group, a formyl group, a formyloxy group, a $C_1$-$C_8$-alkoxycarbonyl, a $C_1$-$C_8$-halogenoalkoxycarbonyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylsulphonyl, a $C_1$-$C_8$-halogenoalkylsulphonyl having 1 to 5 halogen atoms, a $C_1$-$C_8$-alkyl, a $C_1$-$C_8$-cycloalkyl, a $C_1$-$C_8$-halogenoalkyl having 1 to 5 halogen atoms, a $C_1$-$C_8$-halogenocycloalkyl having 1 to 5 halogen atoms, a $C_2$-$C_8$-alkenyl, a $C_2$-$C_8$-alkynyl, a $C_1$-$C_8$-alkoxyalkyl, a $C_1$-$C_8$-halogenoalkoxyalkyl having 1 to 5 halogen atoms;
$R^b$ and $R^c$ independently represent a hydrogen atom, a halogen atom, a cyano, a $C_1$-$C_8$-alkyl, a $C_1$-$C_8$-cycloalkyl, a $C_1$-$C_8$-halogenoalkyl having 1 to 5 halogen atoms, a $C_1$-$C_8$-halogenocycloalkyl having 1 to 5 halogen atoms;
X independently represents a $C_1$-$C_{10}$-alkyl, a $C_1$-$C_{10}$-halogenoalkyl, a halogen atom or a cyano;
n represents 0, 1, 2 or 3;
$L^1$ and $L^2$ independently represent a hydrogen atom, a cyano group, a hydroxy group, an amino group, a formyl group, a formyloxy group, a formylamino group, a carbamoyl group, a N-hydroxycarbamoyl group, a carbamate group, substituted or non-substituted (hydroxyimino)-$C_1$-$C_8$-alkyl group, substituted or non-substituted $C_1$-$C_8$-alkyl, tri($C_1$-$C_8$-alkyl)silyl, substituted or non-substituted tri($C_1$-$C_8$-alkyl)silyl-$C_1$-$C_8$-alkyl, substituted or non-substituted $C_1$-$C_8$-cycloalkyl, substituted or non-substituted tri($C_1$-$C_8$-alkyl)silyl-$C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-alkynyloxy, substituted or non-substituted $C_2$-$C_8$-alkenyloxy, substituted or non-substituted $C_2$-$C_8$-halogenoalkenyloxy having 1 to 5 halogen atoms, substituted or non-substituted $C_2$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted. N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkyloxycarbonyloxy, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylsulphinyl, substituted or non-substituted $C_1$-$C_8$-halogenoalkylsulphinyl having 1 to 5 halogen atoms, substituted or non-substituted $C_1$-$C_8$-alkylsulphonyl, substituted or non-substituted $C_1$-$C_8$-halogenoalkylsulphonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_8$-alkoxyimino)-$C_1$-$C_6$-alkyl, substituted or non-substituted ($C_1$-$C_8$-alkenyloxyimino)-$C_1$-$C_8$-alkyl, substituted or non-substituted ($C_1$-$C_8$-alkynyloxyimino)-$C_1$-$C_8$-alkyl, (2-oxopyrrolidin-1-yl) $C_1$-$C_8$-alkyl, (2-oxopyrrolidin-1-yl) $C_1$-$C_8$-halogenoalkyl having 1 to 5 halogen atoms, (2-oxopiperidin-1-yl) $C_1$-$C_8$-alkyl, (2-oxopiperidin-1-yl) $C_1$-$C_8$-halogenoalkyl having 1 to 5 halogen atoms, (2-oxoazepan-1-yl) $C_1$-$C_8$-alkyl, (2-oxoazepan-1-yl) $C_1$-$C_8$-halogenoalkyl having 1 to 5 halogen atoms, substituted or non-substituted (benzyloxyimino)-$C_1$-$C_8$-alkyl;

$L^1$ and $L^2$ can form together a saturated or unsaturated, aromatic or non-aromatic, substituted or non-substituted 4-, 5-, 6- or 7-membered, N-including heterocycle comprising up to 4 heteroatoms independently selected in the list consisting of N, O, S;

as well as salts, N-oxides, metallic complexes, metalloidic complexes and optically active or geometric isomers thereof; provided that the following compound is excluded: 4-[2-(ethylamino)-4-pyridinyl]-N-[5-(-piperazinyl)-2-pyridinyl]-2-pyrimidinamine.

Any of the compounds according to the present invention may exist in one or more optical or chiral isomeric form depending on the number of asymmetric centres in the compound. The invention thus relates equally to all optical isomers and to any racemic or scalemic mixtures thereof (the term "scalemic" denotes a mixture of enantiomers in different proportions), and to the mixtures of any potential stereoisomers, in any proportion. Diastereoisomers or optical isomers can be separated according to any methods known per se by the man ordinary skilled in the art.

Any of the compounds according to the present invention may also exist in one or more geometric isomeric form depending on the number of double bond within the compound. The invention thus equally relates to any geometric isomer and to any possible mixtures thereof, in any proportion. Geometric isomers can be separated according to any method known per se by the man ordinary skilled in the art.

Any compound of formula (I) according to the invention wherein Y represents a hydroxy group, a sulphenyl group or an amino group can exist in a tautomeric form resulting from the shift of the proton of said hydroxy group, sulphenyl group or amino group respectively. Such tautomeric forms are also part of the present invention. Generally, any tautomeric form of a compound of formula (I) according to the invention wherein Y represents a hydroxy group, a sulphenyl group or an amino group, as well as the tautomeric forms of the compounds which can optionally be used as intermediates in the preparation processes according to the invention are also part of the present invention.

According to the invention, the following generic terms are generally used with the following meanings:
halogen means fluorine, chlorine, bromine or iodine;
heteroatom can be nitrogen, oxygen or sulphur;
unless indicated otherwise, a group or a substituent that is substituted according to the invention can be linear or branched as well as substituted by one or more of the following groups or atoms: a halogen atom, a nitro group, a hydroxy group, a cyano group, an amino group, a sulphenyl group, a pentafluoro-$\lambda^6$-sulphenyl group, a formyl group, a formyloxy group, a formylamino group, a carbamoyl group, a N-hydroxycarbamoyl group, a carbamate group, a (hydroxyimino)-$C_1$-$C_6$-alkyl group, a $C_1$-$C_8$-alkyl, a tri($C_1$-$C_8$-alkyl)silyl-$C_1$-$C_8$-alkyl, $C_1$-$C_8$-cycloalkyl, tri($C_1$-$C_8$-alkyl)silyl-$C_1$-$C_8$-cycloalkyl, a $C_1$-$C_8$-halogenoalkyl having 1 to 5 halogen atoms, a $C_1$-$C_8$-halogenocycloalkyl having 1 to 5 halogen atoms, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulphenyl, a $C_1$-$C_8$-halogenoalkylsulphenyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms, a $C_1$-$C_8$-alkylaminosulfamoyl, a di-$C_1$-$C_8$-alkylaminosulfamoyl, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_8$-alkynyloxyimino)-$C_1$-$C_6$-alkyl, a 2-oxopyrrolidin-1-yl, (benzyloxyimino)-$C_1$-$C_6$-alkyl, $C_1$-$C_8$-alkoxyalkyl, $C_1$-$C_8$-halogenoalkoxyalkyl having 1 to 5 halogen atoms, benzyloxy, benzylsulphenyl, benzylamino, phenoxy, phenylsulphenyl, or phenylamino.

Preferred compounds of formula (I) according to the invention are those wherein Het represents a saturated or unsaturated, aromatic or non-aromatic heterocycle selected in the list consisting of:

Het-1

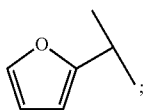

Het-2

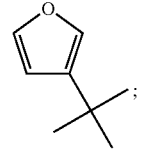

Het-3

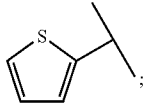

Het-4

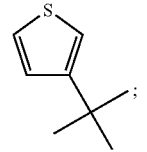

Het-5

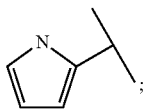

Het-6

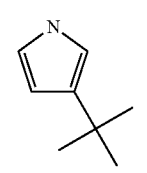

-continued

Het-7

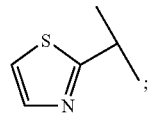

Het-8

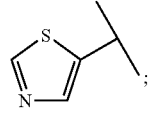

Het-9

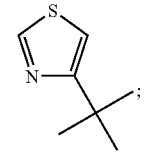

Het-10

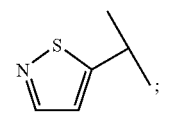

Het-11

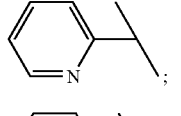

Het12

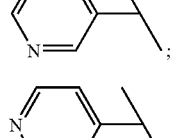

Het13

Other preferred compounds of formula (I) according to the invention are those wherein Y represents a halogen atom, a cyano group, a formylamino group, a carbamoyl group, a substituted or non-substituted (hydroxyimino)-$C_1$-$C_6$-alkyl group, a substituted or non-substituted $C_1$-$C_8$-alkyl, a substituted or non-substituted tri($C_1$-$C_8$-alkyl)silyl, a substituted or non-substituted $C_1$-$C_8$-cycloalkyl, a substituted or non-substituted $C_1$-$C_8$-alkoxy, a substituted or non-substituted $C_1$-$C_8$-halogenoalkoxy having 1 to 5 halogen atoms, a substituted or non-substituted a $C_1$-$C_8$-halogenoalkyl having 1 to 5 halogen atoms, a substituted or non-substituted $C_1$-$C_8$-alkylcarbonylamino. More preferably, Y represents a halogen atom, a cyano group, a formylamino group, a carbamoyl group, a substituted or non-substituted (hydroxyimino)-$C_1$-$C_6$-alkyl group, a substituted or non-substituted $C_1$-$C_8$-alkyl, a substituted or non-substituted tri($C_1$-$C_8$-alkyl)silyl, a substituted or non-substituted $C_1$-$C_8$-cycloalkyl, a substituted or non-substituted $C_1$-$C_8$-alkoxy, a substituted or non-substituted $C_1$-$C_8$-halogenoalkoxy having 1 to 5 halogen atoms, a substituted or non-substituted a $C_1$-$C_6$-halogenoalkyl having 1 to 5 halogen atoms.

Other preferred compounds of formula (I) according to the invention are those wherein p represents 0, 1 or 2. More preferably, p represents 1.

Other preferred compounds of formula (I) according to the invention are those wherein $R^a$ represents a hydrogen atom.

Other preferred compounds of formula (I) according to the invention are those wherein $R^b$ and $R^c$ independently represent a hydrogen atom or a halogen atom. More preferably, $R^b$ and $R^c$ represent a hydrogen atom.

Other preferred compounds of formula (I) according to the invention are those wherein n represents 0.

Other preferred compounds of formula (I) according to the invention are those wherein $L^1$ and $L^2$ independently represent a hydrogen atom, a cyano group, a hydroxy group, an amino group, a formyl group, a formyloxy group, a formylamino group, substituted or non-substituted (hydroxyimino)-$C_1$-$C_6$-alkyl group, substituted or non-substituted $C_1$-$C_8$-alkyl, tri($C_1$-$C_8$-alkyl)silyl, substituted or non-substituted $C_1$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylcarbonyl, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkyloxycarbonyloxy, substituted or non-substituted $C_1$-$C_8$-alkylsulphonyl, substituted or non-substituted $C_1$-$C_8$-halogenoalkylsulphonyl having 1 to 5 halogen atoms, (2-oxopyrrolidin-1-yl) $C_1$-$C_8$-alkyl, (2-oxopyrrolidin-1-yl) $C_1$-$C_8$-halogenoalkyl having 1 to 5 halogen atoms, (2-oxopiperidin-1-yl) $C_1$-$C_8$-alkyl, (2-oxopiperidin-1-yl) $C_1$-$C_8$-halogenoalkyl having 1 to 5 halogen atoms, (2-oxoazepan-1-yl) $C_1$-$C_8$-alkyl, (2-oxoazepan-1-yl) $C_1$-$C_8$-halogenoalkyl having 1 to 5 halogen atoms; when $L^1$ and $L^2$ form together a substituted or non-substituted, 4-, 5-, 6- or 7-membered heterocycle comprising up to 4 heteroatoms selected in the list consisting of N, O, S, $L^1$ and $L^2$ independently represent a substituted or non-substituted 2-oxopyrrolidin-1-yl or a substituted or non-substituted 2-oxo-1,3-oxazolidin-3-yl.

More preferred compounds of formula (I) according to the invention are those wherein $L^1$ and $L^2$ independently represent a hydrogen atom or a linear or branched, substituted or non-substituted $C_1$-$C_8$-alkyl, for example a ($C_1$-$C_8$-alkoxy)-$C_1$-$C_8$-alkyl.

The above mentioned preferences with regard to the substituents of the compounds of formula (I) according to the invention can be combined in various manners, either individually, partially or entirely. These combinations of preferred features thus provide sub-classes of compounds according to the invention. Examples of such sub-classes of preferred compounds according to the invention can combine:

preferred features of Het with preferred features of one or more of Y, p, $R^a$, $R^b$, $R^c$, X, n, $L^1$ and $L^2$;
preferred features of Y with preferred features of one or more of Het, p, $R^a$, $R^b$, $R^c$, X, n, $L^1$ and $L^2$;
preferred features of p with preferred features of one or more of Het, Y, $R^a$, $R^b$, $R^c$, X, n, $L^1$ and $L^2$;
preferred features of $R^a$ with preferred features of one or more of Het, Y, p, $R^b$, $R^c$, X, n, $L^1$ and $L^2$;
preferred features of $R^b$ with preferred features of one or more of Het, Y, p, $R^a$, $R^c$, X, n, $L^1$ and $L^2$;
preferred features of $R^c$ with preferred features of one or more of Het, Y, p, $R^a$, $R^b$, X, n, $L^1$ and $L^2$;
preferred features of X with preferred features of one or more of Het, Y, p, $R^a$, $R^b$, $R^c$, n, $L^1$ and $L^2$;
preferred features of n with preferred features of one or more of Het, Y, p, $R^a$, $R^b$, $R^c$, X, $L^1$ and $L^2$;
preferred features of $L^1$ with preferred features of one or more of Het, Y, p, $R^a$, $R^b$, $R^c$, X, n and $L^2$;
preferred features of $L^2$ with preferred features of one or more of Het, Y, p, $R^a$, $R^b$, $R^c$, X, n and $L^1$.

In these combinations of preferred features of the substituents of the compounds according to the invention, the said preferred features can also be selected among the more preferred features of each of Het, Y, p, $R^a$, $R^b$, $R^c$, X, n, $L^1$ and $L^2$ so as to form most preferred subclasses of compounds according to the invention.

The present invention also relates to a process for the preparation of compounds of formula (I). Thus according to a further aspect of the present invention, there is provided a process P1 for the preparation of a compound of formula (I) as herein-defined, as illustrated by the following reaction scheme:

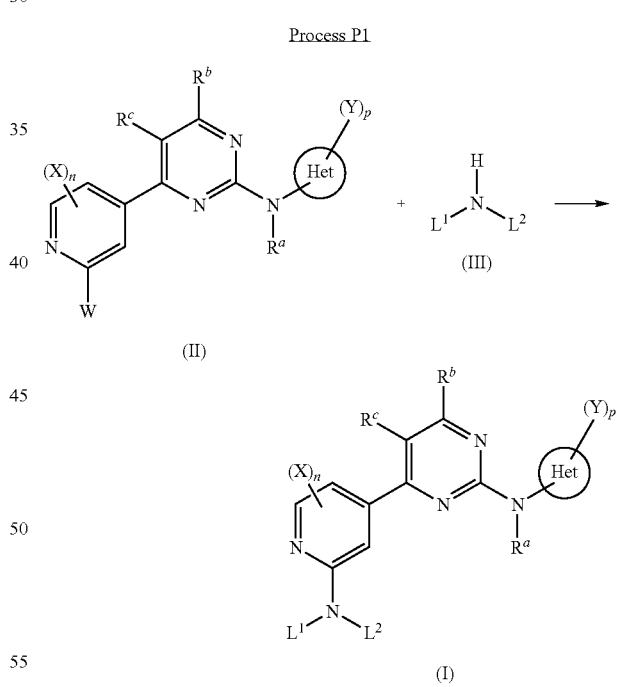

wherein
W represents a leaving group such as a halogen atom, a $C_1$-$C_6$ alkylsulfonate, a $C_1$-$C_6$ haloalkylsulfonate; a substituted or non-substituted phenylsulfonate and
X, Y, n, p, $R^a$, $R^b$, $R^c$, $L^1$, $L^2$, Het, being as herein-defined; and that comprises
reacting a compound of formula (II) with an amino derivative of formula (III) in order to yield a compound of formula (I), optionally in the presence of a catalyst, preferably a transition metal catalyst, such as a copper salt, preferably a copper(I) salt for example copper(I) chloride, copper(I) cyanide, such as palladium salts or complexes for example palladium (II) chloride, palladium (II) acetate, tetrakis-(triphenylphosphine) palladium(0), bis-(triphenylphosphine) palladium dichloride (II), tris(dibenzylideneacetone)dipalladium(0), bis(dibenzylideneacetone) palladium(0), or 1,1'-bis(diphenylphosphino)ferrocene-palladium (II) chloride. As an alternative the palladium complex is directly generated in the reaction mixture by separately adding to the reaction mixture a palladium salt and a complex ligand such as a phosphine, for example triethylphosphine, tri-tert-butylphosphine, tricyclohexylphosphine, 2-(dicyclohexylphosphine)biphenyl, 2-(di-tert-butylphosphin) biphenyl, 2-(dicyclohexylphosphine)-2'-(N,N-dimethylamino)-biphenyl, triphenylphosphine, tris-(o-tolyl)phosphine, sodium 3-(diphenylphosphino) benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine)ethane, 1,4-bis-(dicyclohexylphosphine)butane, 1,2-bis-(dicyclohexylphosphine) ethane, 2-(dicyclohexylphosphine)-2'-(N,N-dimethylamino)-biphenyl, bis(diphenylphosphino) ferrocene, tris-(2,4-tert-butylphenyl)-phosphite, (R)-(−)-1-[(S)-2-(diphenylphosphino)ferrocenyl]ethyldi-tert-butylphosphine, (S)-(+)-1-[(R)-2-(diphenylphosphino)ferrocenyl] ethyldicyclohexylphosphine, (R)-(+1-[(S)-2-(diphenylphosphino)ferrocenyl] ethyldicyclohexylphosphine, (S)-(+)-1-[(R)-2-(diphenylphosphino)ferrocenyl]ethyldi-t-butylphosphine, optionally in the presence of a base, such as an inorganic or an organic base; preferably an alkaline earth metal or alkali metal hydrides, hydroxides, amides, alcoholates, acetates, carbonates or hydrogen carbonates, such as sodium hydride, sodium amide, lithium diisopropylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, cesium carbonate or ammonium carbonate; and also tertiary amines, such as trimethylamine, triethylamine (TEA), tributylamine, N,N-dimethylaniline, N,N-dimethyl-benzylamine, N,N-diisopropyl-ethylamine (DIPEA), pyridine, N-methylpiperidine, N-methylmorpholine, N,N-dimethylaminopyridine, diazabicyclooctane (DABCO), diazabicyclononene (DBN) or diazabicycloundecene (DBU);

Depending on the respective definitions of X, Y, n, p, $R^a$, $R^b$, $R^c$, Het, amino-pyrimidine derivatives of formula (II) may be prepared by various processes.

Accordingly, there is provided a process A according to the invention for the preparation of a compound of formula (II) wherein $R^a$ represents a hydrogen atom;
X, Y, n, p, $R^b$, $R^c$, Het being as herein-defined; and comprising a first step according to reaction scheme A-1:

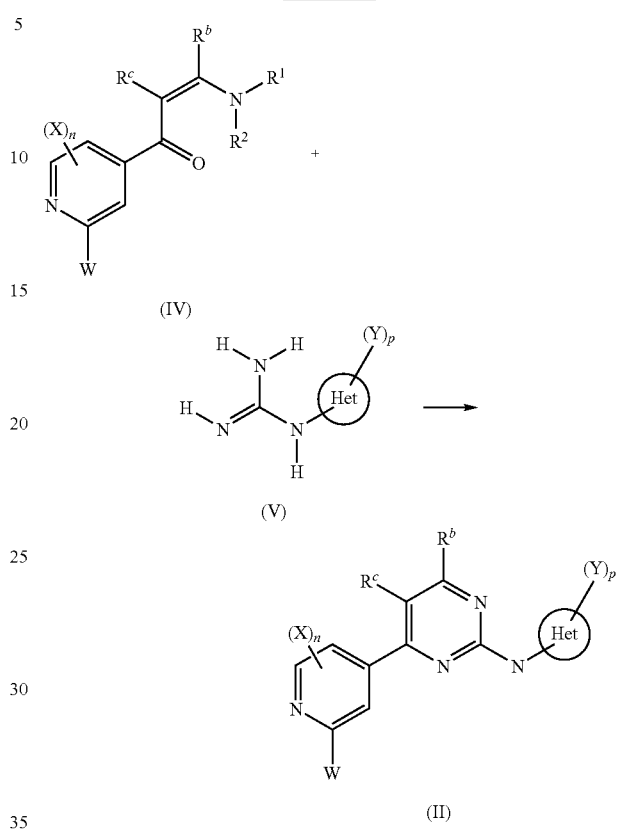

wherein
W, X, Y, n, p, $R^b$, $R^c$, Het, being as herein-defined;
$R^1$ and $R^2$ are independently a $C_1$-$C_8$-alkyl group, $R^1$ and $R^2$ can form together a substituted or non-substituted, 4-, 5-, 6- or 7-membered heterocycle comprising up to 4 heteroatoms selected in the list consisting of N, O, S;

that comprises the formation of the pyrimidine moiety by condensation, at a temperature of from −50° C. to 200° C., of a compound of formula (IV), optionally in the presence of a base such as an inorganic or an organic base, preferably an alkaline earth metal or alkali metal hydrides, hydroxides, amides, alcoholates, acetates, carbonates or hydrogen carbonates, such as sodium hydride, sodium amide, lithium diisopropylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, cesium carbonate or ammonium carbonate; and also tertiary amines, such as trimethylamine, triethylamine (TEA), tributylamine, N,N-dimethylaniline, N,N-dimethyl-benzylamine, N,N-diisopropyl-ethylamine (DIPEA), pyridine, N-methylpiperidine, N-methylmorpholine, N,N-dimethylaminopyridine, diazabicyclooctane (DABCO), diazabicyclononene (DBN) or diazabicycloundecene (DBU); with a guanidine or a guanidine salt derivative of formula (V) to yield a compound of formula (II).

Alternatively, there is provided a process B according to the invention for the preparation of a compound of formula (II) wherein W, X, Y, n, p, $R^a$, $R^b$, $R^c$, Het being as herein-defined; and comprising a first step according to reaction scheme B-1:

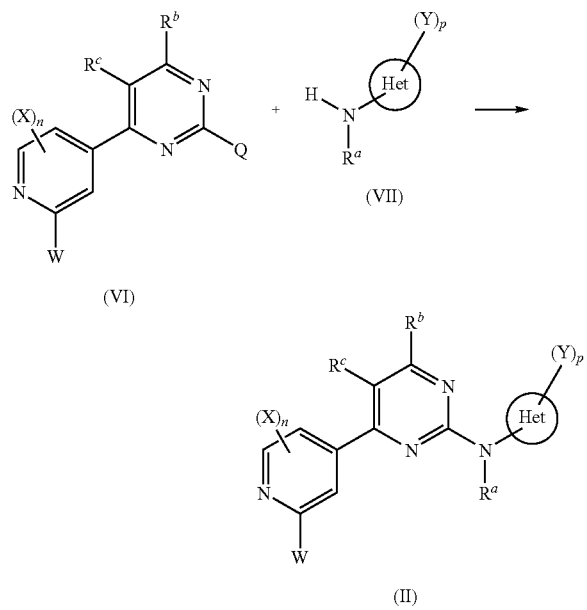

wherein
W, X, Y, n, p, $R^a$, $R^b$, $R^c$, Het being as herein-defined;
Q represents a hydrogen atom or a leaving group such as a halogen atom, a $C_1$-$C_6$ alkylsulphenyl, a $C_1$-$C_6$ haloalkylsulphenyl; a substituted or non-substituted phenylsulphenyl, a $C_1$-$C_6$ alkylsulfonate, a $C_1$-$C_6$ haloalkylsulfonate; a substituted or non-substituted phenylsulfonate and that comprises reacting a compound of formula (VI) with an amino derivative of formula (VII) in order to yield a compound of formula (II), optionally in the presence of a catalyst, preferably a transition metal catalyst, such as palladium salts or complexes for example palladium (II) chloride, palladium (II) acetate, tetrakis-(triphenylphosphine) palladium(0), bis-(triphenylphosphine) palladium dichloride (II), tris(dibenzylideneacetone)dipalladium(0), bis(dibenzylideneacetone) palladium(0), or 1,1'-bis(diphenylphosphino)ferrocene-palladium (II) chloride. As an alternative the palladium complex is directly generated in the reaction mixture by separately adding to the reaction mixture a palladium salt and a complex ligand such as a phosphine, for example triethylphosphine, tri-tert-butylphosphine, tricyclohexylphosphine, 2-(dicyclohexylphosphine)biphenyl, 2-(di-tert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino)benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine)ethane, 1,4-bis-(dicyclohexylphosphine) butane, 1,2-bis-(dicyclohexylphosphine)ethane, 2-(dicyclohexylphosphine)-2'-(N,N-dimethylamino)-biphenyl, bis(diphenylphosphino)ferrocene, tris-(2,4-tert-butylphenyl)-phosphite, (R)-(−)-1-[(S)-2-(diphenylphosphino) ferrocenyl]ethyldi-tert-butylphosphine, (S)-(+)-1-[(R)-2-(diphenylphosphino)ferrocenyl]ethyldicyclohexylphosphine, (R)-(−)-1-[(S)-2-(diphenylphosphino)ferrocenyl]ethyldicyclohexylphosphine, (S)-(+)-1-[(R)-2-(diphenylphosphino)ferrocenyl]ethyldi-t-butylphosphine, optionally in the presence of an organo-metallic reagent such as an organo-lithium reagent, for example n-butyl lithium, methyl lithium, phenyl lithium or an organo-magnesium halide reagent (Grignard reagent) such as isopropyl magnesium halide more preferably such as isopropyl magnesium chloride, optionally in the presence of a base, such as an inorganic or an organic base, preferably an alkaline earth metal or alkali metal hydrides, hydroxides, amides, alcoholates, acetates, carbonates or hydrogen carbonates, such as sodium hydride, sodium amide, lithium diisopropylamide, 2,2,6,6-tetramethylpiperidylmagnesium chloride, lithium hexamethyldisilazide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, cesium carbonate or ammonium carbonate; and also tertiary amines, such as to trimethylamine, triethylamine (TEA), tributylamine, N,N-dimethylaniline, N,N-dimethyl-benzylamine, N,N-diisopropyl-ethylamine (DIPEA), pyridine, N-methylpiperidine, N-methylmorpholine, N,N-dimethylaminopyridine, diazabicyclooctane (DABCO), diazabicyclononene (DBN) or diazabicycloundecene (DBU), optionally in the presence of a metallic salt such as an alkaline earth metal salt, an alkali metal salt, a transition metal salt such as a lithium salt, preferably a lithium halide, more preferably lithium chloride, such as a copper salt, preferably a copper(I) salt such as copper(I) chloride, copper(I) cyanide, in the presence of an oxidative agent such as oxygen, 3,3',5,5'-tetra-tert-butyl-diphenoquinone, 2,3-dichloro-5,6-dicyano-1,4-benzoquinone (DDQ), and 2,3,5,6-tetrachloro-1,4-benzoquinone (chloranil).

Alternatively, there is provided a process C according to the invention for the preparation of a compound of formula (II) wherein W, X, Y, n, p, $R^a$, $R^b$, $R^c$, Het, being as herein-defined; and comprising
a first step according to reaction scheme C-1:

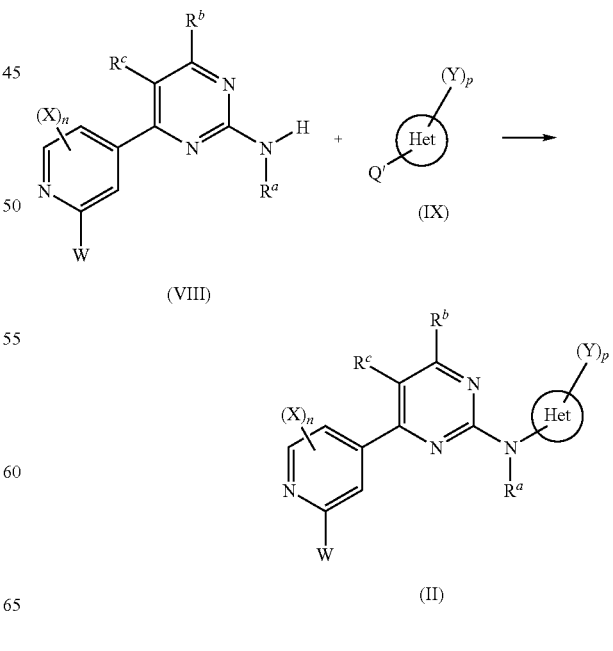

wherein
W, X, Y, n, p, $R^a$, $R^b$, $R^c$, Het, being as herein-defined;
Q' represents a leaving group such as a halogen atom, a $C_1$-$C_6$ alkylsulphenyl, a $C_1$-$C_6$ haloalkylsulphenyl; a substituted or non-substituted phenylsulphenyl a $C_1$-$C_6$-alkylsulfonate, a $C_1$-$C_6$ haloalkylsulfonate; a substituted or non-substituted phenylsulfonate, and that comprises reacting an amino derivative of formula (VIII) with a compound of formula (IX) in order to yield a compound of formula (II), optionally in the presence of a catalyst, preferably a transition metal catalyst, such as palladium salts or complexes for example palladium (II) chloride, palladium (II) acetate, tetrakis-(triphenylphosphine) palladium(0), bis-(triphenylphosphine) palladium dichloride (II), tris(dibenzylideneacetone)dipalladium(0), bis(dibenzylideneacetone) palladium(0), or 1,1'-bis(diphenylphosphino)ferrocene-palladium (II) chloride. As an alternative the palladium complex is directly generated in the reaction mixture by separately adding to the reaction mixture a palladium salt and a complex ligand such as a phosphine, for example triethylphosphine, tri-tert-butylphosphine, tricyclohexylphosphine, 2-(dicyclohexylphosphine)biphenyl, 2-(di-tert-butylphosphin)biphenyl, 2-(dicyclohexylphosphine)-2'-(N,N-dimethylamino)-biphenyl, triphenylphosphine, tris-(o-tolyl)phosphine, sodium 3-(diphenylphosphino)benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine)ethane, 1,4-bis-(dicyclohexylphosphine)butane, 1,2-bis-(dicyclohexylphosphine)ethane, 2-(dicyclohexylphosphine)-2'-(N,N-dimethylamino)-biphenyl, bis(diphenylphosphino)ferrocene, tris-(2,4-tert-butylphenyl)-phosphite, (R)-(-)-1-[(S)-2-(diphenylphosphino)ferrocenyl]ethyldi-tert-butylphosphine, (S)-(-)-1-[(R)-2-(diphenylphosphino)ferrocenyl]ethyldicyclohexylphosphine, (R)-(-)-1-[(S)-2-(diphenylphosphino)ferrocenyl]ethyldicyclohexylphosphine, (S)-(+)-1-[(R)-2-(diphenylphosphino)ferrocenyl]ethyldi-t-butylphosphine, optionally in the presence of an organo-metallic reagent such as an organo-lithium reagent for example n-butyl lithium, methyl lithium, phenyl lithium or an organo-magnesium halide reagent (Grignard reagent) such as isopropyl magnesium halide for example isopropyl magnesium chloride, optionally in the presence of a base, such as an inorganic or an organic base; preferably an alkaline earth metal or alkali metal hydrides, hydroxides, amides, alcoholates, acetates, carbonates or hydrogen carbonates, such as sodium hydride, sodium amide, lithium diisopropylamide, 2,2,6,6-tetramethylpiperidylmagnesium chloride, lithium hexamethyldisilazide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, cesium carbonate or ammonium carbonate; and also tertiary amines, such as trimethylamine, triethylamine (TEA), tributylamine, N,N-dimethylaniline, N,N-dimethyl-benzylamine, N,N-diisopropyl-ethylamine (DIPEA), pyridine, N-methylpiperidine, N-methylmorpholine, N,N-dimethylaminopyridine, diazabicyclooctane (DABCO), diazabicyclononene (DBN) or diazabicycloundecene (DBU), optionally in the presence of a metallic salt such as an alkaline earth metal salt, an alkali metal salt, a transition metal salt such as a lithium salt, preferably a lithium halide, more preferably lithium chloride, such as a copper salt, preferably a copper(I) salt such as copper(I) chloride, copper(I) cyanide, in the presence of an oxidative agent such as oxygen, 3,3',5,5'-tetra-tert-butyldiphenoquinone, 2,3-dichloro-5,6-dicyano-1,4-benzoquinone (DDQ), and 2,3,5,6-tetrachloro-1,4-benzoquinone (chloranil).

Suitable solvents for carrying out processes P1, A, B and C according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

When carrying out processes P1, A, B and C according to the invention, the reaction temperatures can independently be varied within a relatively wide range. Generally, processes according to the invention are carried out at temperatures between −80° C. and 250° C.

Processes P1, A, B and C according to the invention are generally independently carried out under atmospheric pressure. However, in each case, it is also possible to operate under elevated or reduced pressure.

Work-up is carried out by customary methods. Generally, the reaction mixture is treated with water and the organic phase is separated off and, after drying, concentrated under reduced pressure. If appropriate, the remaining residue can be freed by customary methods, such as chromatography or recrystallization, from any impurities that may still be present.

Compounds according to the invention can be prepared according to the above described process. It will nevertheless be understood that, on the basis of his general knowledge and of available publications, the skilled worker will be able to adapt these processes according to the specifics of each of the compounds according to the invention that is desired to be synthesized.

Still in a further aspect, the present invention relates to compounds of formula (II) useful as intermediate compounds or materials for the process of preparation according to the invention. The present invention thus provides compounds of formula (II)

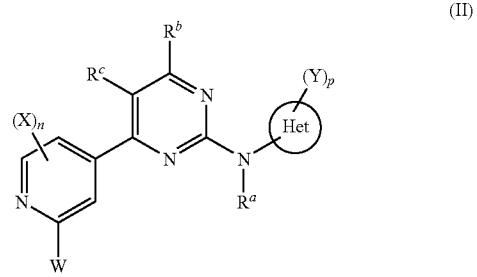

(II)

wherein
W represents a leaving group such as a halogen atom, a $C_1$-$C_6$ alkylsulfonate, a $C_1$-$C_6$ haloalkylsulfonate; a substituted or non-substituted phenylsulfonate and
X, Y, n, p, $R^a$, $R^b$, $R^c$, Het, being as herein-defined.

In a further aspect, the present invention also relates to a fungicide composition comprising an effective and non-phytotoxic amount of an active compound of formula (I).

The expression "effective and non-phytotoxic amount" means an amount of composition according to the invention which is sufficient to control or destroy the fungi present or liable to appear on the crops, and which does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials, which are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic, organic or inorganic compound with which the active compound of formula (I) is combined or associated to make it easier to apply, notably to the parts of the plant. This support is thus generally inert and should be agriculturally acceptable. The support may be a solid or a liquid. Examples of suitable supports include days, natural or synthetic silicates, silica, resins, waxes, solid fertilisers, water, alcohols, in particular butanol, organic solvents, mineral and plant oils and derivatives thereof. Mixtures of such supports may also be used.

The composition according to the invention may also comprise additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active compound and/or the inert support are water-insoluble and when the vector agent for the application is water. Preferably, surfactant content may be comprised from 5% to 40% by weight of the composition.

Optionally, additional components may also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention may contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions which are ready to be applied to the plant or seed to be treated by means of a suitable device, such as a spraying or dusting device, but also concentrated commercial compositions which must be diluted before application to the crop.

The compounds according to the invention can also be mixed with one or more insecticide, fungicide, bactericide, attractant, acaricide or pheromone active substance or other compounds with biological activity. The mixtures thus obtained have normally a broadened spectrum of activity. The mixtures with other fungicide compounds are particularly advantageous.

Examples of suitable fungicide mixing partners may be selected in the following lists:

B1) a compound capable to inhibit the nucleic acid synthesis like benalaxyl, benalaxyl-M, bupirimate, chiralaxyl, clozylacon, dimethirimol, ethirimol, furalaxyl, hymexazol, metalaxyl-M, ofurace, oxadixyl, oxolinic acid;

B2) a compound capable to inhibit the mitosis and cell division like benomyl, carbendazim, diethofencarb, fuberidazole, pencycuron, thiabendazole thiophanate-methyl, zoxamide;

B3) a compound capable to inhibit the respiration for example
as CI-respiration inhibitor like diflumetorim;
as CII-respiration inhibitor like boscalid, carboxin, fenfuram, flutolanil, furametpyr, mepronil, oxycarboxine, penthiopyrad, thifluzamide;
as CIII-respiration inhibitor like azoxystrobin, cyazofamid, dimoxystrobin, enestrobin, famoxadone, fenamidone, fluoxastrobin, kresoxim-methyl, metominostrobin, orysastrobin, pyraclostrobin, picoxystrobin, trifloxystrobin;

B4) a compound capable of to act as an uncoupler like dinocap, fluazinam;

B5) a compound capable to inhibit ATP production like fentin acetate, fentin chloride, fentin hydroxide, silthiofam;

B6) a compound capable to inhibit AA and protein biosynthesis like andoprim, blasticidin-S, cyprodinil, kasugamycin, kasugamycin hydrochloride hydrate, mepanipyrim, pyrimethanil;

B7) a compound capable to inhibit the signal transduction like fenpiclonil, fludioxonil, quinoxyfen;

B8) a compound capable to inhibit lipid and membrane synthesis like chlozolinate, iprodione, procymidone, vinclozolin, pyrazophos, edifenphos, iprobenfos (IBP), isoprothiolane, tolclofos-methyl, biphenyl, iodocarb, propamocarb, propamocarb-hydrochloride;

B9) a compound capable to inhibit ergosterol biosynthesis like fenhexamid, azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazol, penconazole, propiconazole, prothioconazole, simeconazole, tebuconazole, tetraconazole, triadimefon, triadimenol, triticonazole, uniconazole, voriconazole, imazalil, imazalil sulfate, oxpoconazole, fenarimol, flurprimidol; nuarimol, pyrifenox, triforine, pefurazoate, prochloraz, triflumizole, viniconazole, aldimorph, dodemorph, dodemorph acetate, fenpropimorph, tridemorph, fenpropidin, spiroxamine, naftifine, pyributicarb, terbinafine;

B10) a compound capable to inhibit cell wall synthesis like benthiavalicarb, bialaphos, dimethomorph, flumorph, iprovalicarb, polyoxins, polyoxorim, validamycin A;

B11) a compound capable to inhibit melanine biosynthesis like carpropamid, diclocymet, fenoxanil, phthalide, pyroquilon, tricyclazole;

B12) a compound capable to induce a host defense like acibenzolar-S-methyl, probenazole, tiadinil;

B13) a compound capable to have a multisite action like captafol, captan, chlorothalonil, copper preparations such as copper hydroxide, copper naphthenate, copper oxychloride, copper sulphate, copper oxide, oxine-copper and Bordeaux mixture, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, propineb, sulphur and sulphur preparations including calcium polysulphide, thiram, tolylfluanid, zineb, ziram;

B14) a compound selected in the list consisting of: amibromdole, benthiazole, bethoxazin, capsimycin, carvone, chinomethionat, chloropicrin, cufraneb, cyflufenamid, cymoxanil, dazomet, debacarb, diclomezine, dichlorophen, dicloran, difenzoquat, difenzoquat methylsulphate, diphenylamine, ethaboxam, ferimzone, flumetover, flusulfamide, fosetyl-aluminium, fosetyl-calcium, fosetyl-sodium, fluopicolide, fluoroimide, hexachlorobenzene, 8-hydroxyquinoline sulfate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, phosphorous acid and its salts, piperalin, propanosine-sodium, proquinazid, pyrrolnitrine, quintozene, tecloftalam, tecnazene, triazoxide, trichlamid, zarilamid and 2,3,5,6-tetrachloro-4-(methylsulfonyl)-pyridine, N-(4-Chloro-2-nitrophenyl)-N-ethyl-4-methyl-benzenesulfonamide, 2-amino-4-methyl-N-phenyl-5-thiazolecarboxamide, 2-chloro-N-(2,3-dihydro-1,1,3-trimethyl-1H-inden-4-yl)-3-pyridincarboxamide, 3-[5-(4-chlorophenyl)-2,3-dimethylisoxazolidin-3-yl]pyridine, cis-1-(4-chlorophenyl)-2-(1H-1,2,4-triazole-1-yl)-cycloheptanol, methyl 1-(2,3-dihydro-2,2-dimethyl-1H-inden-1-yl)-1H-imidazole-5-carboxylate, 3,4,5-trichloro-2,6-pyridinedicarbonitrile, Methyl 2-[[[cyclopropyl[(4-methoxyphenyl)imino]methyl]thio]methyl]-.alpha.-(methoxymethylene)-benzeneacetate, 4-Chloro-alpha-propynyloxy-N-[2-[3-methoxy-4-(2-propynyloxy)phenyl]ethyl]-benzeneacetamide, (2S)—N-[2-[4-[[3-(4-chlorophenyl)-2-propynyl]oxy]-3-methoxyphenyl]ethyl]-3-methyl-2-[(methylsulfonyl)amino]-butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propyl-benzopyranon-4-one, N-{(Z)-[(cyclopropylmethoxy)imino][6-(difluoromethoxy)-2,3-difluorophenyl]methyl}-2-phenylacetamide, N-(3-ethyl-3,5,5-trimethyl-cyclohexyl)-3-formylamino-2-hydroxy-benzamide, 2-[[[[1-[3(1Fluoro-2-phenylethyl)oxy]phenyl]ethylidene]amino]oxy]methyl]-alpha-(methoxyimino)-N-methyl-alphaE-benzeneacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, 2-(2-{[6-(3-chloro-2-methylphenoxy)-5-fluoropyrimidin-4-yl]oxy}phenyl)-2-(methoxyimino)-N-methylacetamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid.

The composition according to the invention comprising a mixture of a compound of formula (I) with a bactericide compound may also be particularly advantageous. Examples of suitable bactericide mixing partners may be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The compounds of formula (I) and the fungicide composition according to the invention can be used to curatively or preventively control the phytopathogenic fungi of plants or crops.

Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

The method of treatment according to the invention may also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

Among the plants that can be protected by the method according to the invention, mention may be made of: cotton; flax; vine; fruit or vegetable crops such as *Rosaceae* sp. (for instance pip fruit such as apples and pears, but also stonefruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for instance banana trees and plantains), *Rubiaceae* sp., *Theaceae* sp., *Sterculiceae* sp., *Rutaceae* sp. (for instance lemons, oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

Among the diseases of plants or crops that can be controlled by the method according to the invention, mention may be made of:

Powdery mildew diseases such as:
*Blumeria* diseases, caused for example by *Blumeria graminis*;
*Podosphaera* diseases, caused for example by *Podosphaera leucotricha*;

*Sphaerotheca* diseases, caused for example by *Sphaerotheca fuliginea*;
*Uncinula* diseases, caused for example by *Uncinula necator*;
Rust diseases such as:
*Gymnosporangium* diseases, caused for example by *Gymnosporangium sabinae*;
*Hemileia* diseases, caused for example by *Hemileia vastatrix*;
*Phakopsora* diseases, caused for example by *Phakopsora pachyrhizi* or *Phakopsora meibomiae*;
*Puccinia* diseases, caused for example by *Puccinia recondita*;
*Uromyces* diseases, caused for example by *Uromyces appendiculatus*;
Oomycete diseases such as:
*Bremia* diseases, caused for example by *Bremia lactucae*;
*Peronospora* diseases, caused for example by *Peronospora pisi* or *P. brassicae*;
*Phytophthora* diseases, caused for example by *Phytophthora infestans*;
*Plasmopara* diseases, caused for example by *Plasmopara viticola*;
*Pseudoperonospora* diseases, caused for example by *Pseudoperonospora humuli* or
*Pseudoperonospora cubensis*;
*Pythium* diseases, caused for example by *Pythium ultimum*;
Leafspot, leaf blotch and leaf blight diseases such as:
*Alternaria* diseases, caused for example by *Alternaria solani*;
*Cercospora* diseases, caused for example by *Cercospora beticola*;
*Cladiosporum* diseases, caused for example by *Cladiosporium cucumerinum*;
*Cochliobolus* diseases, caused for example by *Cochliobolus sativus*;
*Colletotrichum* diseases, caused for example by *Colletotrichum lindemuthanium*;
*Cycloconium* diseases, caused for example by *Cycloconium oleaginum*;
*Diaporthe* diseases, caused for example by *Diaporthe citri*;
*Elsinoe* diseases, caused for example by *Elsinoe fawcettii*;
*Gloeosporium* diseases, caused for example by *Gloeosporium laeticolor*;
*Glomerella* diseases, caused for example by *Glomerella cingulata*;
*Guignardia* diseases, caused for example by *Guignardia bidwelli*;
*Leptosphaeria* diseases, caused for example by *Leptosphaeria maculans; Leptosphaeria nodorum*;
*Magnaporthe* diseases, caused for example by *Magnaporthe grisea*;
*Mycosphaerella* diseases, caused for example by *Mycosphaerella graminicola; Mycosphaerella arachidicola; Mycosphaerella fijiensis*;
*Phaeosphaeria* diseases, caused for example by *Phaeosphaeria nodorum*;
*Pyrenophora* diseases, caused for example by *Pyrenophora teres*;
*Ramularia* diseases, caused for example by *Ramularia collo-cygni*;
*Rhynchosporium* diseases, caused for example by *Rhynchosporium secalis*;
*Septoria* diseases, caused for example by *Septoria apii* or *Septoria lycopercisi*;
*Typhula* diseases, caused for example by *Typhula incamata*;
*Venturia* diseases, caused for example by *Venturia inaequalis*;

Root and stem diseases such as:
*Corticium* diseases, caused for example by *Corticium graminearum*;
*Fusarium* diseases, caused for example by *Fusarium oxysporum*;
*Gaeumannomyces* diseases, caused for example by *Gaeumannomyces graminis*;
*Rhizoctonia* diseases, caused for example by *Rhizoctonia solani*;
*Tapesia* diseases, caused for example by *Tapesia acuformis*;
*Thielaviopsis* diseases, caused for example by *Thielaviopsis basicola*;
Ear and panicle diseases such as:
*Alternaria* diseases, caused for example by *Alternaria* spp.;
*Aspergillus* diseases, caused for example by *Aspergillus flavus*;
*Cladosporium* diseases, caused for example by *Cladosporium* spp.;
*Claviceps* diseases, caused for example by *Claviceps purpurea*;
*Fusarium* diseases, caused for example by *Fusarium culmorum*;
*Gibberella* diseases, caused for example by *Gibberella zeae*;
*Monographella* diseases, caused for example by *Monographella nivalis*;
Smut and bunt diseases such as:
*Sphacelotheca* diseases, caused for example by *Sphacelotheca reiliana*;
*Tilletia* diseases, caused for example by *Tilletia caries*;
*Urocystis* diseases, caused for example by *Urocystis occulta*;
*Ustilago* diseases, caused for example by *Ustilago nuda*;
Fruit rot and mould diseases such as:
*Aspergillus* diseases, caused for example by *Aspergillus flavus*;
*Botrytis* diseases, caused for example by *Botrytis cinerea*;
*Penicillium* diseases, caused for example by *Penicillium expansum*;
*Sclerotinia* diseases, caused for example by *Sclerotinia sclerotiorum*;
*Verticilium* diseases, caused for example by *Verticilium alboatrum*;
Seed and soilborne decay, mould, wilt, rot and damping-off diseases such as:
*Fusarium* diseases, caused for example by *Fusarium culmorum*;
*Phytophthora* diseases, caused for example by *Phytophthora cactorum*;
*Pythium* diseases, caused for example by *Pythium ultimum*;
*Rhizoctonia* diseases, caused for example by *Rhizoctonia solani*;
*Sclerotium* diseases, caused for example by *Sclerotium rolfsii*;
*Microdochium* diseases, caused for example by *Microdochium nivale*;
Canker, broom and dieback diseases such as:
*Nectria* diseases, caused for example by *Nectria galligena*;
Blight diseases such as:
*Monilinia* diseases, caused for example by *Monilinia taxa*;
Leaf blister or leaf curl diseases such as:
*Taphrina* diseases, caused for example by *Taphrina deformans*;
Decline diseases of wooden plants such as:
Esca diseases, caused for example by *Phaemoniella clamydospora*;
*Eutypa* dyeback, caused for example by *Eutypa rata*;

Dutch elm disease, caused for example by *Ceratocystsc ulmi;*
Diseases of flowers and Seeds such as:
*Botrytis* diseases, caused for example by *Botrytis cinerea;*
Diseases of tubers such as:
*Rhizoctonia* diseases, caused for example by *Rhizoctonia solani.*

The fungicide composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The fungicide composition according to the invention may also be used in the treatment of genetically modified organisms with the compounds according to the invention or the agrochemical compositions according to the invention. Genetically modified plants are plants into genome of which a heterologous gene encoding a protein of interest has been stably integrated. The expression "heterologous gene encoding a protein of interest" essentially means genes which give the transformed plant new agronomic properties, or genes for improving the agronomic quality of the modified plant.

The compounds or mixtures according to the invention may also be used for the preparation of composition useful to curatively or preventively treat human or animal fungal diseases such as, for example, mycoses, dermatoses, *trichophyton* diseases and candidiases or diseases caused by *Aspergillus* spp., for example *Aspergillus fumigatus.*

The various aspects of the invention will now be illustrated with reference to the following table of compound examples A and the following preparation or efficacy examples.

The following table illustrates in a non-limiting manner examples of compounds according to the invention.

In the following table, M+H (or M−H) means the molecular ion peak, plus or minus 1 a.m.u. (atomic mass unit) respectively, as observed in mass spectroscopy and M (Apcl+) means the molecular ion peak as it was found via positive atmospheric pressure chemical ionisation in mass spectroscopy.

In the following table, the log P values were determined in accordance with EEC Directive 79/831 Annex V.A8 by HPLC (High Performance Liquid Chromatography) on a reversed-phase column (C 18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known log P values (determination of the log P values by the retention times using linear interpolation between two successive alkanones).

The lambda max values were determined in the maxima of the chromatographic signals using the UV spectra from 190 nm to 400 nm.

TABLE A

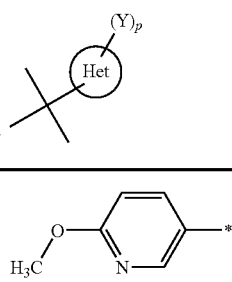

| Example Number | $R^a$ | $L^1$ | $L^2$ | $R^b$ | $R^c$ | (Y)p Het | $X^1$ | $X^2$ | $X^3$ | Measured Mw | log $P_{HCOOH}$ |
|---|---|---|---|---|---|---|---|---|---|---|---|
| 1 | H | H₃C—* | methyl | H | H | 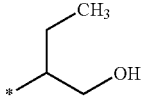 | H | H | H | | 1.24 |
| 2 | H | *CH(CH₃)CH₂OH | H | H | H | 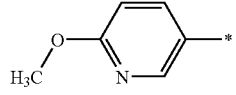 | H | H | H | | 1.35 |

TABLE A-continued
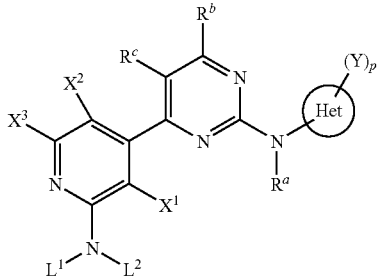
| Example Number | R$^a$ | L$^1$ | L$^2$ | R$^b$ | R$^c$ |  | X$^1$ | X$^2$ | X$^3$ | Measured Mw | log P$_{HCOOH}$ |
|---|---|---|---|---|---|---|---|---|---|---|---|
| 3 | H | 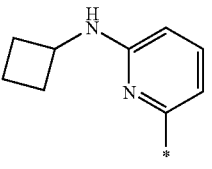 | H | H | H | 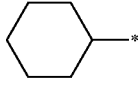 | H | H | H | 194.5 | 1.12 |
| 4 | H | 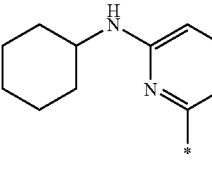 | H | H | H | 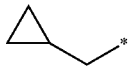 | H | H | H | 444 | 1.70 |
| 5 | H | 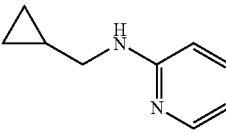 | H | H | H |  | H | H | H | 388 | 0.97 |
| 6 | H | 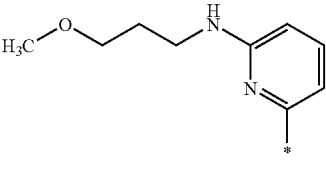 | H | H | H | 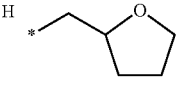 | H | H | H | 424 | 0.83 |
| 7 | H | 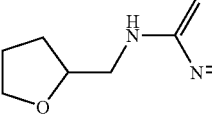 | H | H | H | 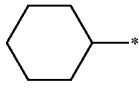 | H | H | H | 225 | 0.86 |
| 8 | H | 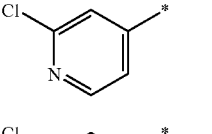 | H | H | Cl |  | H | H | H | 381 | 1.64 |
| 9 | H | 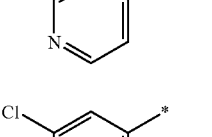 | H | H | Cl |  | H | H | H | 385 | 1.37 |
| 10 | H |  | H | H | Cl | 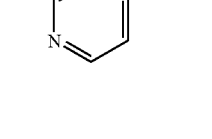 | H | H | H | 369 | 1.66 |

TABLE A-continued

| Example Number | R^a | L^1 | L^2 | R^b | R^c | Het(Y)_p | X^1 | X^2 | X^3 | Measured Mw | log P_{HCOOH} |
|---|---|---|---|---|---|---|---|---|---|---|---|
| 11 | H | cyclobutyl | H | H | H | 2-Cl-pyridin-4-yl | H | H | H | 353 | 1.45 |
| 12 | H | 4-methylpentan-2-yl | H | H | H | 2-Cl-pyridin-4-yl | H | H | H | 369 | 1.72 |
| 13 | H | 2-butyl (sec-butyl w/ ethyl) | H | H | H | 2-Cl-pyridin-4-yl | H | H | H | 369 | 1.64 |
| 14 | H | cyclopentyl | H | H | H | 2-Cl-pyridin-4-yl | H | H | H | 367 | 1.58 |
| 15 | H | cyclohexyl | H | H | H | 2-(cyclohexylamino)pyridin-4-yl | H | H | H | 444 | 1.52 |
| 16 | H | cyclopropylmethyl | H | H | H | 2-(cyclopropylmethylamino)pyridin-6-yl | H | H | H | 388 | 0.96 |
| 17 | H | n-pentyl | H | H | H | 2-(pentylamino)pyridin-4-yl | H | H | H | 418 | 1.57 |
| 18 | H | 3-methylbutan-2-yl | H | H | H | 2-(3-methylbutan-2-ylamino)pyridin-4-yl | H | H | H | 420 | 1.34 |
| 19 | H | cyclobutyl | H | H | H | 2-(cyclobutylamino)pyridin-4-yl | H | H | H | 388 | 1.05 |

TABLE A-continued

| Example Number | R<sup>a</sup> | L<sup>1</sup> | L<sup>2</sup> | R<sup>b</sup> | R<sup>c</sup> | Het (Y)<sub>p</sub> | X<sup>1</sup> | X<sup>2</sup> | X<sup>3</sup> | Measured Mw | log P<sub>HCOOH</sub> |
|---|---|---|---|---|---|---|---|---|---|---|---|
| 20 | H | (1-methylbutyl) | H | H | H | N-(1-methylbutyl)-pyridin-2-yl | H | H | H | 420 | 1.43 |
| 21 | H | (1-ethylpropyl) | H | H | H | N-(1-ethylpropyl)-pyridin-2-yl | H | H | H | 420 | 1.33 |
| 22 | H | cyclopentyl | H | H | H | N-cyclopentyl-pyridin-2-yl | H | H | H | 416 | 1.22 |
| 23 | H | (2-methylbutyl via sec) | H | H | H | N-(sec-butyl)-pyridin-2-yl | H | H | H | 392 | 1.10 |
| 24 | H | (1-ethylpropyl) | H | H | H | 6-chloropyridin-2-yl | H | H | H | 369 | 2.09 |
| 25 | H | (3-methylbutyl) | H | H | H | 6-chloropyrimidin-4-yl | H | H | H | 355 | 2.00 |
| 26 | H | (3-methylbutan-2-yl) | H | H | H | 6-chloropyridin-2-yl | H | H | H | 369 | 2.15 |
| 27 | H | (tetrahydrofuran-2-ylmethyl) | H | H | H | 6-chloropyridin-2-yl | H | H | H | 383 | 1.64 |
| 28 | H | (2-(dimethylamino)propyl) | H | H | H | 6-chloropyridin-2-yl | H | H | H | 384 | 1.42 |

TABLE A-continued

| Example Number | R^a | L^1 | L^2 | R^b | R^c | Het(Y)_p | X^1 | X^2 | X^3 | Measured Mw | log P_{HCOOH} |
|---|---|---|---|---|---|---|---|---|---|---|---|
| 29 | H | CH3CH2CH(CH2OCH3)– | H | H | H | 6-chloropyridin-2-yl | H | H | H | 385 | 1.85 |
| 30 | H | 2-butyl (sec-butyl with ethyl) | H | H | H | 6-(pentan-3-ylamino)pyridin-2-yl | H | H | H | 420 | 1.47 |
| 31 | H | cyclopentyl | H | H | H | 6-(cyclopentylamino)pyridin-2-yl | H | H | H | 208.5 | 1.23 |
| 32 | H | isobutyl (3-methylbutan-2-yl) | H | H | H | 6-(butan-2-ylamino)pyridin-2-yl | H | H | H | 196.5 | 1.23 |
| 33 | H | 3-methylbutan-2-yl | H | H | H | 6-(3-methylbutan-2-ylamino)pyridin-2-yl | H | H | H | 420 | 1.43 |
| 34 | H | 1-methoxybutan-2-yl | H | H | H | 6-(1-methoxybutan-2-ylamino)pyridin-4-yl | H | H | H | 452 | 1.10 |
| 35 | H | 1-methoxypropan-2-yl | H | H | H | 2-chloropyridin-4-yl | H | H | H | 371 | 1.34 |
| 36 | H | oxetan-3-yl | H | H | H | 6-methoxypyridin-3-yl | H | H | H | 351.2 | 1.10 |

TABLE A-continued
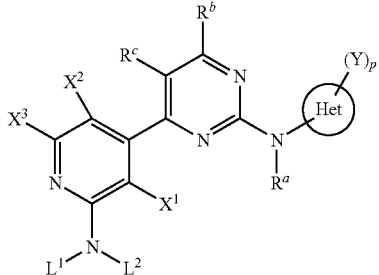
| Example Number | R$^a$ | L$^1$ | L$^2$ | R$^b$ | R$^c$ | Het(Y)$_p$ | X$^1$ | X$^2$ | X$^3$ | Measured Mw | log P$_{HCOOH}$ |
|---|---|---|---|---|---|---|---|---|---|---|---|
| 37* * hydrochloride | H | 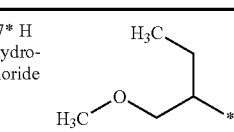 | H | H | H | 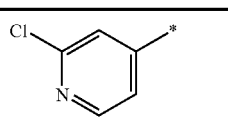 2-Cl-pyridin-4-yl | H | H | H | 385 | 1.49 |
| 38 | H | 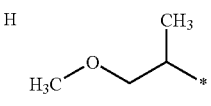 | H | H | H | 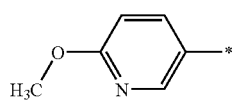 6-methoxypyridin-3-yl | H | H | H | 367.2 | 1.29 |
| 39 | H | 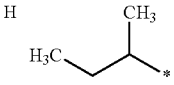 | H | H | H | 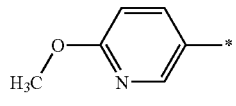 6-methoxypyridin-3-yl | H | H | H | 351 | 1.48 |
| 40 | H | 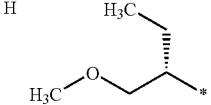 | H | H | H | 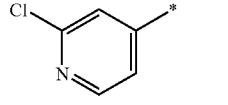 2-Cl-pyridin-4-yl | H | H | H | | |
| 41 | H | 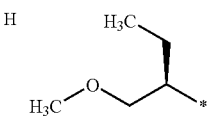 | H | H | H | 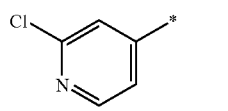 2-Cl-pyridin-4-yl | H | H | H | | |
| 42 | H | 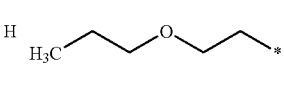 | H | H | H | 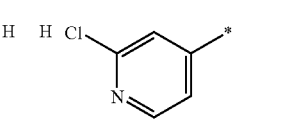 2-Cl-pyridin-4-yl | H | H | H | 385 | |
| 43 | H | 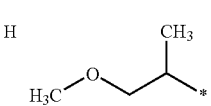 | H | H | H | 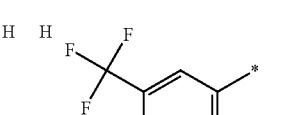 2-CF$_3$-pyridin-4-yl | H | H | H | 405 | |
| 44 | H | 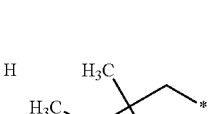 | H | H | H | 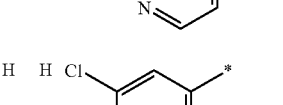 2-Cl-pyridin-4-yl | H | H | H | 385 | |
| 45 | H | 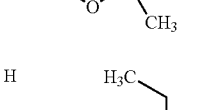 | H | H | H | 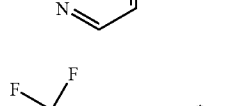 2-CF$_3$-pyridin-4-yl | H | H | H | 419 | |

TABLE A-continued

| Example Number | R$^a$ | L$^1$ | L$^2$ | R$^b$ | R$^c$ | Het(Y)$_p$ | X$^1$ | X$^2$ | X$^3$ | Measured Mw | log P$_{HCOOH}$ |
|---|---|---|---|---|---|---|---|---|---|---|---|
| 46 | H | isobutyl | H | H | H | 2-methoxypyridin-5-yl | H | H | H | 351 | 1.42 |
| 47 | H | 2-methylbutan-1-ol | H | H | H | 2-methoxypyridin-5-yl | H | H | H | 381 | |
| 48 | H | 4-(2-oxopyrrolidin-1-yl)butyl | H | H | H | 2-methoxypyridin-5-yl | H | H | H | 434 | |
| 49 | H | 3-(2-oxopyrrolidin-1-yl)propyl | H | H | H | 2-methoxypyridin-5-yl | H | H | H | 420 | |
| 50 | H | 3-methoxypropyl | H | H | H | 2-methoxypyridin-5-yl | H | H | H | 367 | |
| 51 | H | 2-ethoxyethyl | H | H | H | 2-methoxypyridin-5-yl | H | H | H | 367 | |
| 52 | H | cyclopropylmethyl | H | H | H | 2-methoxypyridin-5-yl | H | H | H | 349 | |
| 53 | H | 3-hydroxypropyl | H | H | H | 2-methoxypyridin-5-yl | H | H | H | 353 | |
| 54 | H | 3,3-dimethylbutyl | H | H | H | 2-methoxypyridin-5-yl | H | H | H | 379 | |
| 55 | H | prop-2-yn-1-yl | H | H | H | 2-methoxypyridin-5-yl | H | H | H | 333 | |

TABLE A-continued

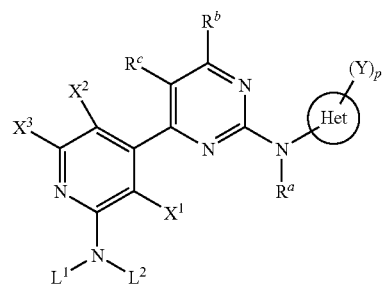

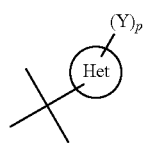

| Example Number | R$^a$ | L$^1$ | L$^2$ | R$^b$ | R$^c$ | Het(Y)$_p$ | X$^1$ | X$^2$ | X$^3$ | Measured Mw | log P$_{HCOOH}$ |
|---|---|---|---|---|---|---|---|---|---|---|---|
| 56 | H | (CH₃)₂CHCH₂- | H | H | H | 2-methoxypyridin-5-yl | H | H | H | 379 | |
| 57 | H | (CH₃)₂CHCH₂- (isobutyl) | H | H | H | 2-methoxypyridin-5-yl | H | H | H | 365 | |
| 58 | H | CH₃CH₂SCH₂CH₂- | H | H | H | 2-methoxypyridin-5-yl | H | H | H | 383 | |
| 59 | H | (CH₃)₂NCH(CH₃)CH₂- | H | H | H | 2-methoxypyridin-5-yl | H | H | H | 380 | |
| 60 | H | NC-CH₂CH₂- | H | H | H | 2-methoxypyridin-5-yl | H | H | H | 348 | |
| 61 | H | HOCH₂C(CH₃)₂CH₂- | H | H | H | 2-methoxypyridin-5-yl | H | H | H | 381 | |
| 62 | H | CH₂=C(CH₃)CH₂- | H | H | H | 2-methoxypyridin-5-yl | H | H | H | 349 | |
| 63 | H | CH₃S(CH₂)₃- | H | H | H | 2-methoxypyridin-5-yl | H | H | H | 383 | |
| 64 | H | HOCH(CH₃)CH₂- | H | H | H | 2-methoxypyridin-5-yl | H | H | H | 353 | |
| 65 | H | CH₃CH(OH)CH₂- | H | H | H | 2-methoxypyridin-5-yl | H | H | H | 367 | |

TABLE A-continued

| Example Number | R$^a$ | L$^1$ | L$^2$ | R$^b$ | R$^c$ | Het-(Y)$_p$ | X$^1$ | X$^2$ | X$^3$ | Measured Mw | log P$_{HCOOH}$ |
|---|---|---|---|---|---|---|---|---|---|---|---|
| 66 | H | H$_3$C-CH(CH$_3$)-O-CH$_2$CH$_2$-* | H | H | H | 2-methoxypyridin-5-yl | H | H | H | 381 | |
| 67 | H | H$_3$C-(CH$_2$)$_4$-CH$_2$-* | H | H | H | 2-methoxypyridin-5-yl | H | H | H | 379 | |
| 68 | H | (CH$_3$)$_2$CH-CH$_2$CH$_2$-* | H | H | H | 2-methoxypyridin-5-yl | H | H | H | 365 | |
| 69 | H | H$_3$C-(CH$_2$)$_2$-CH$_2$-* | H | H | H | 2-methoxypyridin-5-yl | H | H | H | 351 | |
| 70 | H | H$_3$C-S-CH$_2$CH$_2$-* | H | H | H | 2-methoxypyridin-5-yl | H | H | H | 369 | |
| 71 | H | *-CH$_2$-(tetrahydrofuran-2-yl) | H | H | H | 2-methoxypyridin-5-yl | H | H | H | 379 | |
| 72 | H | HO-(CH$_2$)$_3$-CH$_2$-* | H | H | H | 2-methoxypyridin-5-yl | H | H | H | 367 | |
| 73 | H | HO-CH$_2$-CH(CH$_3$)-CH$_2$CH$_2$-* | H | H | H | 2-methoxypyridin-5-yl | H | H | H | 381 | |
| 74 | H | H$_3$C-CH$_2$-O-CH$_2$CH$_2$-* | H | H | H | 2-methoxypyridin-5-yl | H | H | H | 381 | |
| 75 | H | HO-(CH$_2$)$_4$-CH$_2$-* | H | H | H | 2-methoxypyridin-5-yl | H | H | H | 381 | |

TABLE A-continued
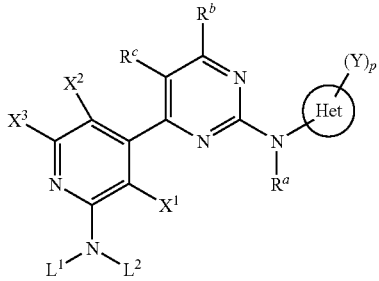
| Example Number | R$^a$ | L$^1$ | L$^2$ | R$^b$ | R$^c$ | 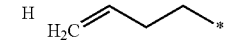 | X$^1$ | X$^2$ | X$^3$ | Measured Mw | log P$_{HCOOH}$ |
|---|---|---|---|---|---|---|---|---|---|---|---|
| 76 | H | 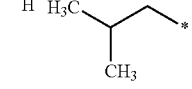 | | H | H | H | 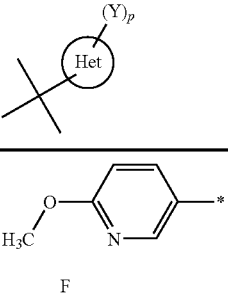 | H | H | H | 349 | |
| 77 | H | 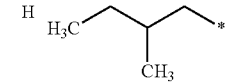 | | H | H | H | 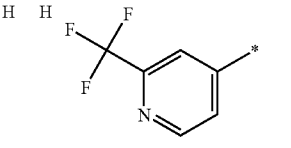 | H | H | H | 389 | |
| 78 | H | 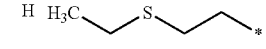 | | H | H | H | 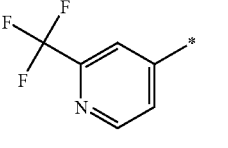 | H | H | H | 403 | |
| 79 | H | 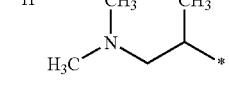 | | H | H | H | 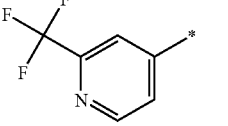 | H | H | H | 421 | |
| 80 | H | 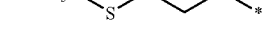 | | H | H | H | 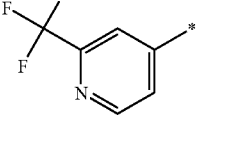 | H | H | H | 418 | |
| 81 | H | 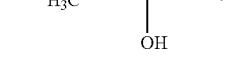 | | H | H | H | 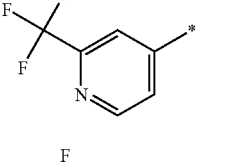 | H | H | H | 421 | |
| 82 | H | 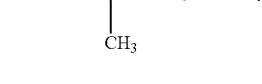 | | H | H | H | 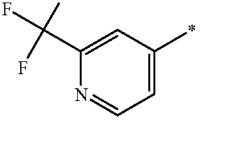 | H | H | H | 405 | |
| 83 | H | | | H | H | H | | H | H | H | 419 | |

TABLE A-continued

| Example Number | Rᵃ | L¹ | L² | Rᵇ | Rᶜ | Het(Y)p | X¹ | X² | X³ | Measured Mw | log P_HCOOH |
|---|---|---|---|---|---|---|---|---|---|---|---|
| 84 | H | (CH₃)₂CHCH₂CH₂-* | H | H | H | 2-(trifluoromethyl)pyridin-4-yl | H | H | H | 403 | |
| 85 | H | (CH₃)₂C=CHCH₂-* | H | H | H | 2-(trifluoromethyl)pyridin-4-yl | H | H | H | 401 | |
| 86 | H | cyclopropyl-CH(CH₃)-* | H | H | H | 2-(trifluoromethyl)pyridin-4-yl | H | H | H | 401 | |
| 87 | H | *-CH₂-(tetrahydrofuran-2-yl) | H | H | H | 2-(trifluoromethyl)pyridin-4-yl | H | H | H | 417 | |
| 88 | H | HO-(CH₂)₄-* | H | H | H | 2-(trifluoromethyl)pyridin-4-yl | H | H | H | 405 | |
| 89 | H | H₃C-CH₂-CH₂-O-CH₂-CH₂-* | H | H | H | 2-(trifluoromethyl)pyridin-4-yl | H | H | H | 419 | |
| 90 | H | H₃C-(CH₂)₅-* | H | H | H | 2-(trifluoromethyl)pyridin-4-yl | H | H | H | 417 | |

TABLE A-continued

[Structure: pyridine with L¹-N-L² at 2-position, X³/X² at 6/5, X¹ at 3, connected at 4-position to pyrimidine bearing R^c (5), R^b (6), and N(R^a)-Het(Y)_p at 2-position]

The $\overset{(Y)_p}{\underset{Het}{\bigcirc}}$ group shown is attached via:

$$\text{—C(CH}_3\text{)}_2\text{—Het(Y)}_p$$

(depicted as tert-carbon linker to Het ring)

| Example Number | R^a | L¹ | L² | R^b | R^c | (Y)_p–Het | X¹ | X² | X³ | Measured Mw | log P_HCOOH |
|---|---|---|---|---|---|---|---|---|---|---|---|
| 91 | H | H₂C=CH–CH₂–CH₂–* | H | H | H | 2-(CF₃)-pyridin-4-yl* | H | H | H | 387 | |
| 92 | H | morpholin-4-yl–CH₂CH₂–* | H | H | H | 2-(CF₃)-pyridin-4-yl* | H | H | H | 446 | |
| 93 | H | *–(CH₂)₄–N(2-oxopyrrolidin-1-yl) | H | H | H | 2-(CF₃)-pyridin-4-yl* | H | H | H | 472 | |
| 94 | H | H₃C–O–CH₂CH₂CH₂–* | H | H | H | 2-(CF₃)-pyridin-4-yl* | H | H | H | 405 | |
| 95 | H | H₃C–CH₂–O–CH₂CH₂–* | H | H | H | 2-(CF₃)-pyridin-4-yl* | H | H | H | 405 | |
| 96 | H | HO–CH₂CH₂CH₂–* | H | H | H | 2-(CF₃)-pyridin-4-yl* | H | H | H | 391 | |
| 97 | H | (H₃C)₃C–CH₂CH₂–* | H | H | H | 2-(CF₃)-pyridin-4-yl* | H | H | H | 417 | |
| 98 | H | (H₃C)₂CH–CH₂–* | H | H | H | 2-Cl-pyridin-4-yl* | H | H | H | 355 | 2.17 |

TABLE A-continued
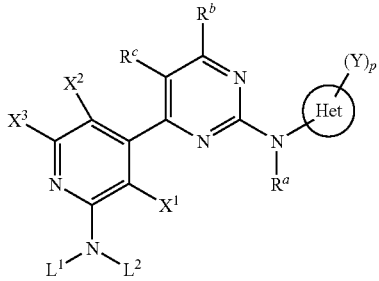
| Example Number | $R^a$ | $L^1$ | $L^2$ | $R^b$ | $R^c$ | 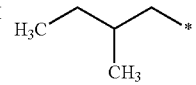 | $X^1$ | $X^2$ | $X^3$ | Measured Mw | log $P_{HCOOH}$ |
|---|---|---|---|---|---|---|---|---|---|---|---|
| 99 | H | 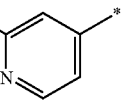 | H | H | Cl | 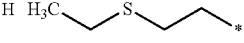 | H | H | H | 369 | 2.17 |
| 100 | H | 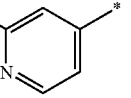 | H | H | Cl | 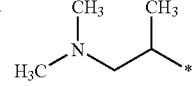 | H | H | H | 387 | 2.17 |
| 101 | H | 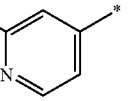 | H | H | Cl | 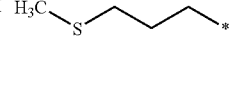 | H | H | H | 384 | 2.17 |
| 102 | H | 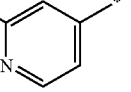 | H | H | Cl | 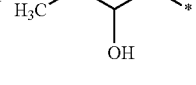 | H | H | H | 387 | |
| 103 | H | 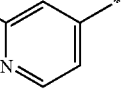 | H | H | Cl | 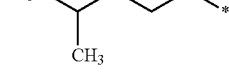 | H | H | H | 371 | |
| 104 | H | 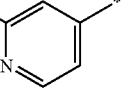 | H | H | Cl |  | H | H | H | 385 | |
| 105 | H | 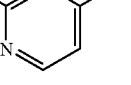 | H | H | Cl | 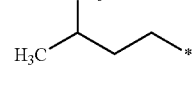 | H | H | H | 383 | |
| 106 | H | 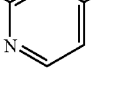 | H | H | Cl | 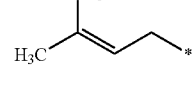 | H | H | H | 369 | |
| 107 | H | 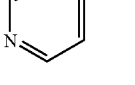 | H | H | Cl | 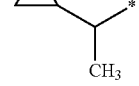 | H | H | H | 367 | |
| 108 | H | 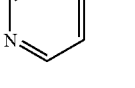 | H | H | Cl | | H | H | H | 367 | |

TABLE A-continued

| Example Number | R$^a$ | L$^1$ | L$^2$ | R$^b$ | R$^c$ | (Het group) | X$^1$ | X$^2$ | X$^3$ | Measured Mw | log P$_{HCOOH}$ |
|---|---|---|---|---|---|---|---|---|---|---|---|
| 109 | H | tetrahydrofuran-2-ylmethyl | H | H | H | 2-Cl-pyridin-4-yl | H | H | H | 383 | |
| 110 | H | H$_3$C-O-(CH$_2$)$_3$-* | H | H | H | 2-Cl-pyridin-4-yl | H | H | H | 371 | |
| 111 | H | HO-(CH$_2$)$_4$-* | H | H | H | 2-Cl-pyridin-4-yl | H | H | H | 371 | |
| 112 | H | H$_2$C=CH-(CH$_2$)$_2$-* | H | H | H | 2-Cl-pyridin-4-yl | H | H | H | 353 | |
| 113 | H | morpholin-4-yl-ethyl-* | H | H | H | 2-Cl-pyridin-4-yl | H | H | H | 412 | |
| 114 | H | 2-oxopyrrolidin-1-yl-butyl-* | H | H | H | 2-Cl-pyridin-4-yl | H | H | H | 438 | |
| 115 | H | H$_3$C-CH$_2$-O-(CH$_2$)$_2$-* | H | H | H | 2-Cl-pyridin-4-yl | H | H | H | 371 | |
| 116 | H | HO-(CH$_2$)$_3$-* | H | H | H | 2-Cl-pyridin-4-yl | H | H | H | 357 | |
| 117 | H | (CH$_3$)$_3$C-CH$_2$-CH$_2$-* | H | H | H | 2-Cl-pyridin-4-yl | H | H | H | 383 | |
| 118 | H | —C(CH$_3$)=N—C(CH$_3$)=N— | | H | H | 2-methoxy-pyridin-5-yl | H | H | H | | 2.11 |

TABLE A-continued

| Example Number | $R^a$ | $L^1$ | $L^2$ | $R^b$ | $R^c$ | Het-(Y)$_p$ | $X^1$ | $X^2$ | $X^3$ | Measured Mw | log $P_{HCOOH}$ |
|---|---|---|---|---|---|---|---|---|---|---|---|
| 119 | H | —CH$_2$CH$_2$CH$_2$CH$_2$— | | H | H | 2-methoxypyridin-5-yl (H$_3$C-O-pyridine) | H | H | H | 349.3 | 1.42 |
| 120 | H | —COCH$_2$CH$_2$CH$_2$— | | H | H | 2-methoxypyridin-5-yl (H$_3$C-O-pyridine) | H | H | H | 363 | 2.17 |

The following examples illustrate in a non-limiting manner the preparation and efficacy of the compounds of formula (I) according to the invention.

Preparation of N-(2-chloropyridin-4-yl)-4-(2-{[1-(methoxymethyl)propyl]amino}pyridin-4-yl)pyrimidin-2-amine (Compound 9) According to Process P1

300 mg of N,4-bis(2-chloropyridin-4-yl)pyrimidin-2-amine (0.94 mmol), 486 mg of 1-methoxybutan-2-amine (4.71 mmol), were heated at 240° C. for 90 minutes under micro-waves irradiation in 0.6 ml of 1-Methyl-2-pyrrolidinone. After cooling, the reaction mixture was poured into 10 ml of dichloromethane, washed twice with 5 ml of water. After drying over magnesium sulfate, filtration and concentration in vacuo, the crude product was chromatographed on silica (ethyl acetate/heptane) to yield 0.72 g of N-(2-chloropyridin-4-yl)-4-(2-{[1-(methoxymethyl)propyl]amino}pyridin-4-yl)pyrimidin-2-amine (yield=19%).
[M+1]=385

Preparation of N,4-bis(2-chloropyridin-4-yl)pyrimidin-2-amine (Compound of formula (II))

Preparation of di-tert-butyl{(Z)-[(2-chloropyridin-4-yl)amino]methylylidene}biscarbamate 20.22 g (0.157 mol) of 4-amino-2-chloropyridine were diluted in triethylamine (67 ml) and dichloromethane (600 ml) at 0-5° C. 47 g of Mercury(II) chloride (0.173 mol) and 50.24 g (0.173 mol) of N,N'-bis(boc)-S-methyl-isothiourea were added to the reaction mixture, which was then stirred at room temperature for 4 days, filtered on a fritted funnel, concentrated in vacuo and chromatographed on silica (Heptane90/AcOEt10) to yield 43.67 g of di-tert-butyl{(Z)-[(2-chloropyridin-4-yl)amino]methylylidene}biscarbamate (yield=71%).
[M+1]=371

Preparation of 1-(2-chloropyridin-4-yl)guanidine bis(trifluoroacetate)

To a solution of 43.67 g (0.117 mol) of di-tert-butyl{(Z)-[(2-chloropyridin-4-yl)amino]methylylidene}biscarbamate in dichloromethane (800 ml) at room temperature were added 81.64 ml of trifluoroacetic acid (1.06 mol). The reaction mixture was stirred at room temperature for 2 days, concentrated in vacuo, triturated with 100 ml of pentane, and upon standing crystallized to yield 51.68 g of 1-(2-chloropyridin-4-yl) guanidine bis(trifluoroacetate) (yield=99%).
[M+1-2*CF$_3$CO$_2$H]=171

Preparation of N,4-bis(2-chloropyridin-4-yl)pyrimidin-2-amine

To a solution of 6.32 g of 1-(2-chloropyridin-4-yl)-3-(dimethylamino)prop-2-en-1-one (30 mmol) in 60 ml of 2-Propanol was added 2.52 g of sodium hydroxide (63 mmol) and 11.96 g of 1-(2-chloropyridin-4-yl)guanidine bis(trifluoroacetate) (30 mmol). The reaction mixture was heated to reflux under stirring for 20 h. After filtration, the precipitate was washed with 100 ml of n-butanol and 120 ml of iPr$_2$O and then air-dried to yield 4.69 g of N,4-bis(2-chloropyridin-4-yl)pyrimidin-2-amine (yield=37%).
[M+1]=318

BIOLOGICAL EXAMPLES

Example A

In Vivo Test on *Peronospora parasitica* (Crucifer Downy Mildew)

The active ingredients tested are prepared by homogenization in a mixture of acetone/Tween/DMSO, then diluted with water to obtain the desired active material concentration.

Cabbage plants (Eminence variety) in starter cups, sown on a 50/50 peat soil-pozzolana substrate and grown at 18-20° C., are treated at the cotyledon stage by spraying with the aqueous suspension described above.

Plants, used as controls, are treated with an aqueous solution not containing the active material. After 24 hours, the plants are contaminated by spraying them with an aqueous suspension of *Peronospora parasitica* spores (50 000 spores per ml). The spores are collected from infected plant.

The contaminated cabbage plants are incubated for 5 days at 20° C., under a humid atmosphere. Grading is carried out 5 days after the contamination, in comparison with the control plants. Under these conditions, good (at least 70%) or total protection is observed at a dose of 500 ppm with the following compounds: 9, 11, 13, 15, 18, 19, 20, 21, 22, 23, 28, 37, 49, 53, 64, 65, 92, 109, 110, 113 and 115.

Example B

In Vivo Test on *Botrytis cinerea* (Grey Mould)

The active ingredients tested are prepared by homogenization in a mixture of acetone/Tween/DMSO, then diluted with water to obtain the desired active material Gherkin plants (Vert petit de Paris variety), sown on a 50/50 peat soil-pozzolana substrate in starter cups and grown at 18-20° C., are treated at the cotyledon Z11 stage by spraying with the active ingredient prepared as described above.

Plants, used as controls, are treated with an aqueous solution not containing the active material. After 24 hours, the plants are contaminated by depositing drops of an aqueous suspension of *Botrytis cinerea* spores (150,000 spores per ml) on upper surface of the leaves. The spores are collected from a 15-day-old culture and are suspended in a nutrient solution composed of:

20 g/L of gelatine;
50 g/L of D-fructose;
2 g/L of $NH_4NO_3$;
1 g/L of $KH_2PO_4$.

The contaminated cucumber plants are settled for 5/7 days in a climatic room at 15-11° C. (day/night) and at 80% relative humidity.

Grading is carried out 5/7 days after the contamination, in comparison with the control plants. Under these conditions, good (at least 70%) or total protection is observed at a dose of 500 ppm with the following compounds: 9, 11, 12, 13, 21, 37, 39, 42, 43, 44, 50, 51, 52, 69, 74, 76 and 106.

Example C

In Vivo Test on *Alternaria brassicae* (Leaf Spot of Crucifers)

The active ingredients tested are prepared by homogenization in a mixture of acetone/tween/DMSO, then diluted with water to obtain the desired active material.

Radish plants (Pernot variety), sown on a 50/50 peat soil-pozzolana substrate in starter cups and grown at 18-20° C., are treated at the cotyledon stage by spraying with the active ingredient prepared as described above.

Plants, used as controls, are treated with the mixture of acetone/tween/water not containing the active material.

After 24 hours, the plants are contaminated by spraying them with an aqueous suspension of *Alternaria brassicae* spores (40,000 spores per $cm^3$). The spores are collected from a 12 to 13 days-old culture.

The contaminated radish plants are incubated for 6-7 days at about 18° C., under a humid atmosphere.

Grading is carried out 6 to 7 days after the contamination, in comparison with the control plants. Under these conditions, good protection (at least 70%) is observed at a dose of 500 ppm with the following compounds: 9, 11, 13, 37, 43, 57, 110 and 115.

Example D

In Vivo Test on *Sphaerotheca fuliqinea* (Cucurbits Powdery Mildew)

The active ingredients tested are prepared by homogenization in a mixture of acetone/tween/DMSO, then diluted with water to obtain the desired active material.

Gherkin plants (Vert petit de Paris variety) in starter cups, sown on a 50/50 peat soil-pozzolana substrate and grown at 20° C./23° C., are treated at the cotyledon Z10 stage by spraying with the aqueous suspension described above. Plants, used as controls, are treated with an aqueous solution not containing the active material.

After 24 hours, the plants are contaminated by spraying them with an aqueous suspension of *Sphaerotheca fuliginea* spores (100 000 spores per ml). The spores are collected from a contaminated plants. The contaminated gherkin plants are incubated at about 20° C./25° C. and at 60/70% relative humidity.

Grading (% of efficacy) is carried out 12 days after the contamination, in comparison with the control plants.

Under these conditions, good (at least 70%) or total protection is observed at a dose of 500 ppm with the following compounds: 9, 13, 37 and 39.

Example E

In Vivo Test on *Pyrenophora teres* (Barley Net Blotch)

The active ingredients tested are prepared by homogenization in a mixture of acetone/Tween/DMSO, then diluted with water to obtain the desired active material concentration.

Barley plants (Express variety), sown on a 50/50 peat soil-pozzolana substrate in starter cups and grown at 12° C., are treated at the 1-leaf stage (10 cm tall) by spraying with the active ingredient prepared as described above.

Plants, used as controls, are treated with an aqueous solution not containing the active material. After 24 hours, the plants are contaminated by spraying them with an aqueous suspension of *Pyrenophora teres* spores (12,000 spores per ml). The spores are collected from a 12-day-old culture. The contaminated barley plants are incubated for 24 hours at about 20° C. and at 100% relative humidity, and then for 12 days at 80% relative humidity.

Grading is carried out 12 days after the contamination, in comparison with the control plants. Under these conditions, good (at least 70%) is observed at a dose of 500 ppm with the following compounds: 9, 10, 11, 12, 13, 21, 36, 37, 38, 39, 43, 44, 45, 46, 51, 52, 57, 60, 62, 64, 65, 66, 68, 69, 76 and 110.

Example F

In Vivo Test on *Puccinia recondita* (Brown Rust)

The active ingredients tested are prepared by homogenization in a mixture of acetone/tween/DMSO, then diluted with water to obtain the desired active material.

Wheat plants (Scipion variety) sown on 50/50 peat soil-pozzolana substrate in starter cups and grown at 12° C., are treated at the 1-leaf stage (10 cm tall) by spraying with the aqueous suspension described above.

Plants, used as controls, are treated with an aqueous solution not containing the active material.

After 24 hours, the plants are contaminated by spraying the leaves with an aqueous suspension of *Puccinia recondita* spores (100,000 spores per ml). The spores are collected from a 10-day-old contaminated wheat and are suspended in water containing 2.5 ml/l of tween 80 10%. The contaminated wheat plants are incubated for 24 hours at 20° C. and at 100% relative humidity, and then for 10 days at 20° C. and at 70% relative humidity.

Grading is carried out 10 days after the contamination, in comparison with the control plants. Under these conditions, good (at least 70%) or total protection is observed at a dose of 500 ppm with the following compounds: 9, 37 and 38.

Example G

In Vivo Test on *Mycosphaerella graminicola* (Wheat Leaf Spot)

The active ingredients tested are prepared by homogenization in a mixture of acetone/tween/DMSO, then diluted with water to obtain the desired active material concentration.

Wheat plants (Scipion variety), sown on a 50/50 peat soil-pozzolana substrate in starter cups and grown at 12° C., are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Mycosphaerella graminicola* spores (500 000 spores per ml). The spores are collected from a 7-day-old culture. The contaminated wheat plants are incubated for 72 hours at 18° C. and at 100% relative humidity, and then for 21 to 28 days at 90% relative humidity.

Grading (% of efficacy) is carried out 21 to 28 days after the contamination, in comparison with the control plants.

Under these conditions, good (at least 70%) or total protection is observed at a dose of 500 ppm with the following compounds: 9, 13, 15, 21, 34, 37, 39, 51, 66 and 74.

Example H

In Vivo Test on *Pyricularia grisea* (Rice Blast)

The active ingredients tested are prepared by homogenization in a mixture of acetone/tween/DMSO, then diluted with water to obtain the desired active material concentration.

Rice plants (Koshihikari variety), sown on a 50/50 peat soil-pozzolana substrate in starter cups and grown at 25° C., are treated at the 2-leaf stage (13-15 cm tall) by spraying with the active ingredient prepared as described above. Plants, used as controls, are treated with the mixture of acetone/tween/DMSO/water not containing the active material.

After 24 hours, the plants are contaminated by spraying them with an aqueous suspension of *Pyricularia grisea* spores (30,000 spores per ml). The spores are collected from a 17-day-old culture and are suspended in water containing 2.5 g/l of gelatin. The contaminated Rice plants are incubated for 72 hours at about 25° C. and at 100% relative humidity, and then for 3 days at 25° C. at 80% relative humidity during the day and 20% relative humidity during the night.

Grading (% of efficacy) is carried out 6 days after the contamination, in comparison with the control plants.

Under these conditions, good (at least 70%) or total protection is observed at a dose of 500 ppm with the following compounds: 9.

The invention claimed is:
1. A compound of formula (I)

$$\text{(I)}$$

wherein
Het is selected from the group consisting of a saturated or unsaturated, aromatic or non-aromatic 4-, 5-, 6- or 7-membered heterocycle comprising up to four heteroatoms which may be the same or different;
each Y is independently selected from the group consisting of a halogen atom, a nitro group, a hydroxy group, an oxo group, a cyano group, an amino group, a sulfenyl group, a pentafluoro-$\lambda^6$-sulfenyl group, a formyl group, a formyloxy group, a formylamino group, a carbamoyl group, a N-hydroxycarbamoyl group, a carbamate group, a substituted or unsubstituted (hydroxyimino)-$C_1$-$C_6$-alkyl group, a substituted or unsubstituted $C_1$-$C_8$-alkyl, a substituted or unsubstituted tri($C_1$-$C_8$-alkyl)silyl, a substituted or non-substituted tri($C_1$-$C_8$-alkyl) silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, a substituted or unsubstituted $C_1$-$C_8$-halogenoalkyl having 1 to 5 halogen atoms, a $C_3$-$C_8$-halogenocycloalkyl having 1 to 5 halogen atoms, a $C_2$-$C_8$-alkenyl, a $C_2$-$C_8$-alkynyl, a $C_2$-$C_8$-alkenyloxy, a $C_2$-$C_8$-alkynyloxy, a $C_1$-$C_8$-alkylamino, a di-$C_1$-$C_8$-alkylamino, a substituted or unsubstituted $C_1$-$C_8$-alkoxy, a substituted or unsubstituted $C_1$-$C_8$-halogenoalkoxy having 1 to 5 halogen atoms, a $C_1$-$C_8$-alkylsulfenyl, a $C_1$-$C_8$-halogenoalkylsulfenyl having 1 to 5 halogen atoms, a $C_2$-$C_8$-halogenoalkenyloxy having 1 to 5 halogen atoms, a $C_3$-$C_8$-halogenoalkynyloxy having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$-alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a substituted or unsubstituted $C_1$-$C_8$alkylcarbonylamino, a $C_1$-$C_8$-halogenoalkylcarbonylamino having 1 to 5 halogen atoms, a $C_1$-$C_8$alkylaminocarbonyloxy, a di-$C_1$-$C_8$-alkylaminocarbonyloxy, a $C_1$-$C_8$-alkyloxycarbonyloxy, a $C_1$-$C_8$-alkylsulfinyl, a $C_1$-$C_8$-halogenoalkylsulfinyl having 1 to 5 halogen atoms, a $C_1$-$C_8$alkylsulfonyl, a $C_1$-$C_8$-halogenoalkylsulfonyl having 1 to 5 halogen atoms, a $C_1$-$C_8$-alkylaminosulfamoyl, a di-$C_1$-$C_8$-alkylaminosulfamoyl, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, a 2-oxopyrrolidin-1-yl, substituted or non-substituted (benzyloxyimino)-$C_1$-$C_6$-alkyl, substituted or non-substituted $C_1$-$C_8$-alkoxyalkyl, substituted or non-substituted $C_1$-$C_8$-halogenoalkoxyalkyl having 1 to 5 halogen atoms, substituted or non-substituted benzyloxy, substituted or non-substituted benzylsulfenyl, substituted or non-substituted benzylamino, substituted or non-substituted phenoxy, substituted or non-substituted phenylsulfenyl, and substituted or non-substituted phenylamino;

p is 0, 1, 2, 3, 4, 5 or 6;

$R^a$ is selected from the group consisting of a hydrogen atom, a cyano group, a formyl group, a formyloxy group, a $C_1$-$C_8$-alkoxycarbonyl, a $C_1$-$C_8$-halogenoalkoxycarbonyl having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylsulfonyl, a $C_1$-$C_8$-halogenoalkylsulfonyl having 1 to 5 halogen atoms, a $C_1$-$C_8$-alkyl, a $C_3$-$C_8$-cycloalkyl, a $C_1$-$C_8$-halogenoalkyl having 1 to 5 halogen atoms, a $C_3$-$C_8$-halogenocycloalkyl having 1 to 5 halogen atoms, a $C_2$-$C_8$-alkenyl, a $C_2$-$C_8$-alkynyl, a $C_1$-$C_8$-alkoxyalkyl, and a $C_1$-$C_8$-halogenoalkoxyalkyl having 1 to 5 halogen atoms;

$R^b$ and $R^c$ are independently selected from the group consisting of a hydrogen atom, a halogen atom, a cyano, a $C_1$-$C_8$-alkyl, a $C_3$-$C_8$-cycloalkyl, a $C_1$-$C_8$-halogenoalkyl having 1 to 5 halogen atoms, and a $C_3$-$C_8$-halogenocycloalkyl having 1 to 5 halogen atoms;

each X is independently selected from the group consisting of a $C_1$-$C_{10}$-alkyl, a $C_1$-$C_{10}$-halogenoalkyl, a halogen atom and a cyano;

n is 0, 1, 2 or 3;

$L^1$ and $L^2$ are independently selected from the group consisting of a hydrogen atom, a cyano group, a hydroxy group, an amino group, a formyl group, a formyloxy group, a formylamino group, a carbamoyl group, a N-hydroxycarbamoyl group, a carbamate group, substituted or non-substituted (hydroxyimino)-$C_1$-$C_6$-alkyl group, substituted or non-substituted $C_1$-$C_8$-alkyl, tri($C_1$-$C_8$-alkyl)silyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$halogenoalkyl having 1 to 5 halogen atoms, substituted or non-substituted $C_3$-$C_8$-halogenocycloalkyl having 1 to 5 halogen atoms a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-alkynyloxy, substituted or non-substituted $C_2$-$C_8$-halogenoalkenyloxy having 1 to 5 halogen atoms, substituted or non-substituted $C_3$-$C_8$-halogenoalkynyloxy having 1 to 5 halogen atoms, substituted or non-substituted $C_1$-$C_8$-alkylcarbonyl, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkyloxycarbonyloxy, substituted or non-substituted $C_1$-$C_8$-alkylsulfenyl, substituted or non-substituted $C_1$-$C_8$-halogenoalkylsulfenyl having 1 to 5 halogen atoms, substituted or non-substituted $C_1$-$C_8$alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, (2-oxopyrrolidin-1-yl) $C_1$-$C_8$-alkyl, (2-oxopyrrolidin-1-yl) $C_1$-$C_8$-halogenoalkyl having 1 to 5 halogen atoms, (2-oxopiperidin-1-yl) $C_1$-$C_8$-alkyl, (2-oxopiperidin-1-yl) $C_1$-$C_8$-halogenoalkyl having 1 to 5 halogen atoms, (2-oxoazepan-1-yl) $C_1$-$C_8$-alkyl, (2-oxoazepan-1-yl) $C_1$-$C_8$-halogenoalkyl having 1 to 5 halogen atoms, and substituted or non-substituted (benzyloxyimino)-$C_1$-$C_6$-alkyl; or $L^1$ and $L^2$ can form together a saturated or unsaturated, aromatic or non-aromatic, substituted or non-substituted 4-, 5-, 6- or 7-membered, N-including heterocycle comprising up to 4 heteroatoms independently selected from the group consisting of N, O, and S; or a salt, N-oxide, or optically active or geometric isomer thereof.

2. The compound of claim 1 wherein Het is a saturated or unsaturated, aromatic or non-aromatic heterocycle selected from the group consisting of:

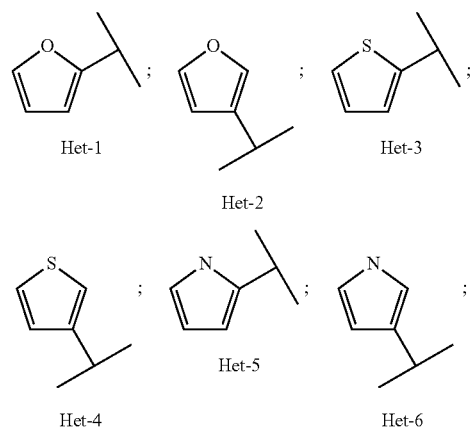

Het-1; Het-2; Het-3; Het-4; Het-5; Het-6

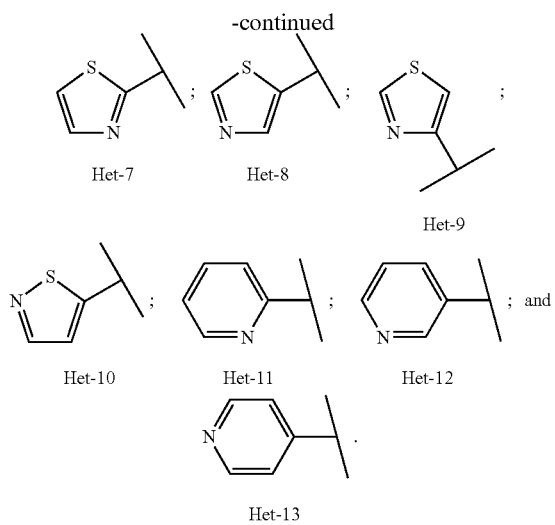

3. The compound of claim 1 wherein each Y is independently selected from the group consisting of a halogen atom, a cyano group, a formylamino group, a carbamoyl group, a substituted or non-substituted (hydroxyimino)-$C_1$-$C_6$-alkyl group, a substituted or non-substituted $C_1$-$C_8$-alkyl, a substituted or non-substituted tri($C_1$-$C_8$-alkyl)silyl, a substituted or non-substituted $C_3$-$C_8$-cycloalkyl, a substituted or non-substituted $C_1$-$C_8$-alkoxy, a substituted or non-substituted $C_1$-$C_8$-halogenoalkoxy having 1 to 5 halogen atoms, a substituted or non-substituted a $C_1$-$C_8$-halogenoalkyl having 1 to 5 halogen atoms, and a substituted or non-substituted $C_1$-$C_8$-alkylcarbonylamino.

4. The compound of claim 1 wherein each Y is independently selected from the group consisting of a halogen atom, a cyano group, a formylamino group, a carbamoyl group, a substituted or non-substituted (hydroxyimino)-$C_1$-$C_6$-alkyl group, a substituted or non-substituted $C_1$-$C_8$-alkyl, a substituted or non-substituted tri($C_1$-$C_8$-alkyl)silyl, a substituted or non-substituted $C_3$-$C_8$cycloalkyl, a substituted or non-substituted $C_1$-$C_8$alkoxy, a substituted or non-substituted $C_1$-$C_8$-halogenoalkoxy having 1 to 5 halogen atoms, and a substituted or non-substituted a $C_1$-$C_8$ halogenoalkyl having 1 to 5 halogen atoms.

5. The compound of claim 1 wherein p is 0, 1 or 2.

6. The compound of claim 1 wherein p is 1.

7. The compound of claim 1 wherein $R^a$ is a hydrogen atom.

8. The compound of claim 1 wherein $R^b$ and $R^c$ are independently selected from the group consisting of a hydrogen atom and a halogen atom.

9. The compound of claim 1 wherein $R^b$ and $R^c$ are both hydrogen atoms.

10. The compound of claim 1 wherein n is 0.

11. The compound of claim 1 wherein $L^1$ and $L^2$ are independently selected from the group consisting of a hydrogen atom, a cyano group, a hydroxy group, an amino group, a formyl group, a formyloxy group, a formylamino group, substituted or non-substituted (hydroxyimino)-$C_1$-$C_6$-alkyl group, substituted or non-substituted $C_1$-$C_8$-alkyl, tri($C_1$-$C_8$-alkyl)silyl, substituted or non-substituted $C_3$-$C_8$: cycloalkyl, substituted or non-substituted $C_1$-$C_8$-halogenoalkyl having 1 to 5 halogen atoms, substituted or non-substituted $C_3$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylcarbonyl, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$alkylaminocarbonyloxy, substituted or non-substituted di-$C_1$-$C_8$-alkylaminocarbonyloxy, substituted or non-substituted $C_1$-$C_8$-alkyloxycarbonyloxy, substituted or non-substituted $C_1$-$C_8$-alkylsulfonyl, substituted or non-substituted $C_1$-$C_8$-halogenoalkylsulfonyl having 1 to 5 halogen atoms, (2-oxopyrrolidin-1-yl) $C_1$-$C_8$-alkyl, (2-oxopyrrolidin-1-yl) $C_1$-$C_8$-halogenoalkyl having 1 to 5 halogen atoms, (2-oxopiperidin-1-yl) $C_1$-$C_8$-alkyl, (2-oxopiperidin-1-yl) $C_1$-$C_8$-halogenoalkyl having 1 to 5 halogen atoms, (2-oxoazepan-1-yl) $C_1$-$C_8$-alkyl, (2-oxoazepan-1-yl) $C_1$-$C_8$-halogenoalkyl having 1 to 5 halogen atoms; or when $L^1$ and $L^2$ form together a substituted or non-substituted, 4-, 5-, 6- or 7-membered heterocycle comprising up to 4 heteroatoms selected from the group consisting of N, O, S, $L^1$ and $L^2$ are independently selected from the group consisting of a substituted or non-substituted 2-oxopyrrolidin-1-yl and a substituted or non-substituted 2-oxo-1,3-oxazolidin-3-yl.

12. The compound of claim 1 wherein $L^1$ and $L^2$ are independently selected from the group consisting of a hydrogen atom and a linear or branched, substituted or non-substituted $C_1$-$C_8$-alkyl.

13. A fungicide composition comprising, as an active ingredient, an effective amount of the compound of claim 1 and an agriculturally acceptable support, carrier or filler.

14. A method for controlling phytopathogenic fungi of crops comprising applying an agronomically effective and substantially non-phytotoxic quantity of the compound of claim 1 to the soil where plants grow or are capable of growing, to the leaves or the fruit of plants or to the seeds of plants.

15. A method for controlling phytopathogenic fungi of crops comprising applying an agronomically effective and substantially non-phytotoxic quantity of the composition of claim 13 to the soil where plants grow or are capable of growing, to the leaves or the fruit of plants or to the seeds of plants.

* * * * *